(12) United States Patent
Brenner et al.

(10) Patent No.: US 8,114,626 B2
(45) Date of Patent: Feb. 14, 2012

(54) YEAST STRAIN AND METHOD FOR USING THE SAME TO PRODUCE NICOTINAMIDE RIBOSIDE

(75) Inventors: Charles Brenner, Lyme, NH (US);
Peter Belenky, Enfield, NH (US);
Katrina L. Bogan, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 330 days.

(21) Appl. No.: 12/411,586

(22) Filed: Mar. 26, 2009

(65) Prior Publication Data
US 2009/0202680 A1 Aug. 13, 2009

Related U.S. Application Data

(60) Continuation-in-part of application No. 11/542,832, filed on Oct. 4, 2006, which is a division of application No. 11/113,701, filed on Apr. 25, 2005, now abandoned, which is a continuation-in-part of application No. PCT/US2005/004337, filed on Feb. 9, 2005.

(60) Provisional application No. 60/543,347, filed on Feb. 10, 2004.

(51) Int. Cl.
*A23L 1/28* (2006.01)
*C12N 1/14* (2006.01)
*C12P 21/02* (2006.01)

(52) U.S. Cl. .... 435/61; 435/256.1; 435/71.1; 435/254.1

(58) Field of Classification Search .................... None
See application file for complete search history.

(56) References Cited

U.S. PATENT DOCUMENTS

| | | | |
|---|---|---|---|
| 2003/0086933 A1 | 5/2003 | Burke et al. | 424/181.1 |
| 2006/0229265 A1 | 10/2006 | Milburn et al. | 514/43 |

OTHER PUBLICATIONS

Gingrich et al., Codehydrogenase I and Other Pyridinium Compounds as V-Factor for *Hemophilus influenzae* and *H. parainfluenzae*, 1994, J. Bacteriolo. 47:535-550.
Leder et al., "Synthesis of Nicotinamide Mononucleotide by Human Erythrocytes in Vitro", 1951 J. Biol. Chem. 189:889-899.
Sasiak et al., "Purification and Properties of a Human Nicotinamide Ribonucleoside Kinase", Archives of Biochemistry and Biophysics 1996 333(2):414-418.
Saunders et al., "Tiazofurin is Phosphorylated by Three Enzymes from Chinese Hamster Ovary Cells", Cancer Research 1990, 50:5269-5274.
Shifrine et al., "Bacteriology—A Growth Factor for *Haemophilus* Species secreted by a Pseudomonad" 1960 Nature 187:613.
NCBI Accession No. CAG61927 [gi:49528270] Apr. 17, 2005.
NCBI Accession No. NP_060351 [gi:8923530] Apr. 22, 2005.
NCBI Accession No. NP_733778 [gi:24762248] Apr. 23, 2005.
NCBI Accession No. NM_017881 [gi:8923529] Apr. 22, 2005.
NCBI Accession No. AK000566 [gi:7020748] Sep. 13, 2003.
NCBI Accession No. BC001366 [gi:33876100] Jun. 29, 2004.
NCBI Accession No. BC036804 [gi:22477870] Mar. 25, 2004.
NCBI Accession No. BC026243 [gi:20072207] Mar. 25, 2004.
NCBI Accession No. NM_170678 [gi:24762247] Apr. 23, 2005.
Holdsworth et al., A fraction derived from brewer's yeast inhibits cholesterol synthesis by rat liver preparation in vitro. Br. J. Nutr. 1991 65, 285-299.
Yalowitz et al., "Modulation of Cytotoxicity of Benzamide Riboside by Expression of NMN Adenylyltransferase", Current Medicinal Chemistry 2002 9:749-758.
Heine et al. "The significance of tryptophan in human nutrition". Amino acids (1995) 9: 191-205.
Albala-Hurtado et al. Determination of water-soluble vitamins in infant milk by high-performance liquid chromatography Journal of chromatography A, 778 (1997) 247-253.
Beata Wielgus-Kutrowska et al. Nicotinamide Riboside, an Unusual, Non-Typical, Substrate of Purified Purine-Nucleoside Phosphorylases. European Journal of Biochemistry vol. 243 Issue 1-2, pp. 408-414.FEBS 1997.

*Primary Examiner* — Kagnew H Gebreyesus
(74) *Attorney, Agent, or Firm* — Licata & Tyrrell P.C.

(57) ABSTRACT

The present invention embraces a fungal strain deficient in nicotinamide riboside import and salvage and use thereof for producing nicotinamide riboside. Methods for producing nicotinamide riboside and a nicotinamide riboside-supplemented food product using the strain of the invention are also provided.

11 Claims, 1 Drawing Sheet

YEAST STRAIN AND METHOD FOR USING THE SAME TO PRODUCE NICOTINAMIDE RIBOSIDE

This application is a continuation-in-part of U.S. patent application Ser. No. 11/542,832, filed Oct. 4, 2006, which is a divisional of U.S. patent application Ser. No. 11/113,701, filed Apr. 25, 2005 now abandoned, which is a continuation-in-part of PCT/US2005/004337, filed Feb. 9, 2005, which claims benefit of U.S. Provisional Patent Application Ser. No. 60/543,347, filed Feb. 10, 2004, the contents of which are incorporated herein by reference in their entireties.

This invention was made in the course of research sponsored by the National Science Foundation, grant number MCB-0822581, and the National Institutes of Health, grant number T32GM008704. The U.S. government has certain rights in this invention.

INTRODUCTION

Background of the Invention

Nicotinic acid (NA), nicotinamide (Nam) and nicotinamide riboside (NR) constitute three salvageable NAD$^+$ precursor vitamins in yeast. NA is imported by the high affinity major facilitator superfamily (MSF) type transporter Tna1 (Llorente & Dujon (2000) *FEBS Lett.* 475:237-41; Klebl, et al. (2000) *FEBS Lett.* 481:86-7). However, not all NA import is Tna1-dependent and at concentrations above 1 μM NA, Tna1-independent import is detectable (Llorente & Dujon (2000) supra). NA is converted to NAD$^+$ via the 3-step Preiss-Handler pathway (Preiss & Handler (1958) *J. Biol. Chem.* 233:488-92; Preiss & Handler (1958) *J. Biol. Chem.* 233:493-500). Nam is converted to NA by the nicotinamidase (Pnc1) (Ghislain, et al. (2002) *Yeast* 19:215-24; Anderson, et al. (2003) *Nature* 423:181-5), for entry into Preiss-Handler salvage. A Nam transporter has not been identified.

SUMMARY OF THE INVENTION

The present invention features an isolated fungal strain deficient in nicotinamide riboside import and salvage. In one embodiment, the strain does not express Nicotinamide Riboside Kinase 1 (Nrk1), Uridine Hydrolase 1 (Urh1), Purine Nucleoside Phosphorylase (Pnp1), and Nicotinamide Riboside Transporter 1 (Nrt1). In another embodiment, the strain secretes at least 8 mg/L nicotinamide riboside. In a further embodiment, the fungus is selected from the group consisting of *Saccharomyces, Schizosaccharomiyces, Kluveromyces, Aspergillus* and *Pichia*. In a specific embodiment, the fungus is *Saccharomyces cerevisiae*.

The present invention also embraces a method for producing nicotinamide riboside by culturing the fungal strain of the invention in culture medium and recovering nicotinamide riboside from the medium. In one embodiment, the culture medium further includes nicotinic acid or nicotinamide. In another embodiment, the fungal strain is cultured to an optical density of at least 3. In a particular embodiment, the nicotinamide riboside is recovered by solubilizing nicotinamide riboside from the medium with methanol and subjecting the nicotinamide riboside to column chromatography.

A method for producing a nicotinamide riboside-supplemented food product is also provided. According to this method, a fermentable substrate is fermented in the presence of the fungal strain of the invention thereby producing a nicotinamide riboside supplemented food product. A nicotinamide riboside supplemented food product fermented in the presence of the fungal strain of the invention is also provided. In some embodiments, the food product is wine, beer, cider, kvass, root beer, soy sauce or bread.

BRIEF DESCRIPTION OF THE DRAWINGS

FIG. 1 shows the measured absorbance of fractions collected from preparative SP-SEPHADEX chromatography. Salt concentration is depicted below the x-axis. An HPLC chromatogram of each fraction was obtained and selected traces are included as the eight smallest inlays. NR eluted between fraction 27 and 36.

DETAILED DESCRIPTION OF THE INVENTION

Figure 1:
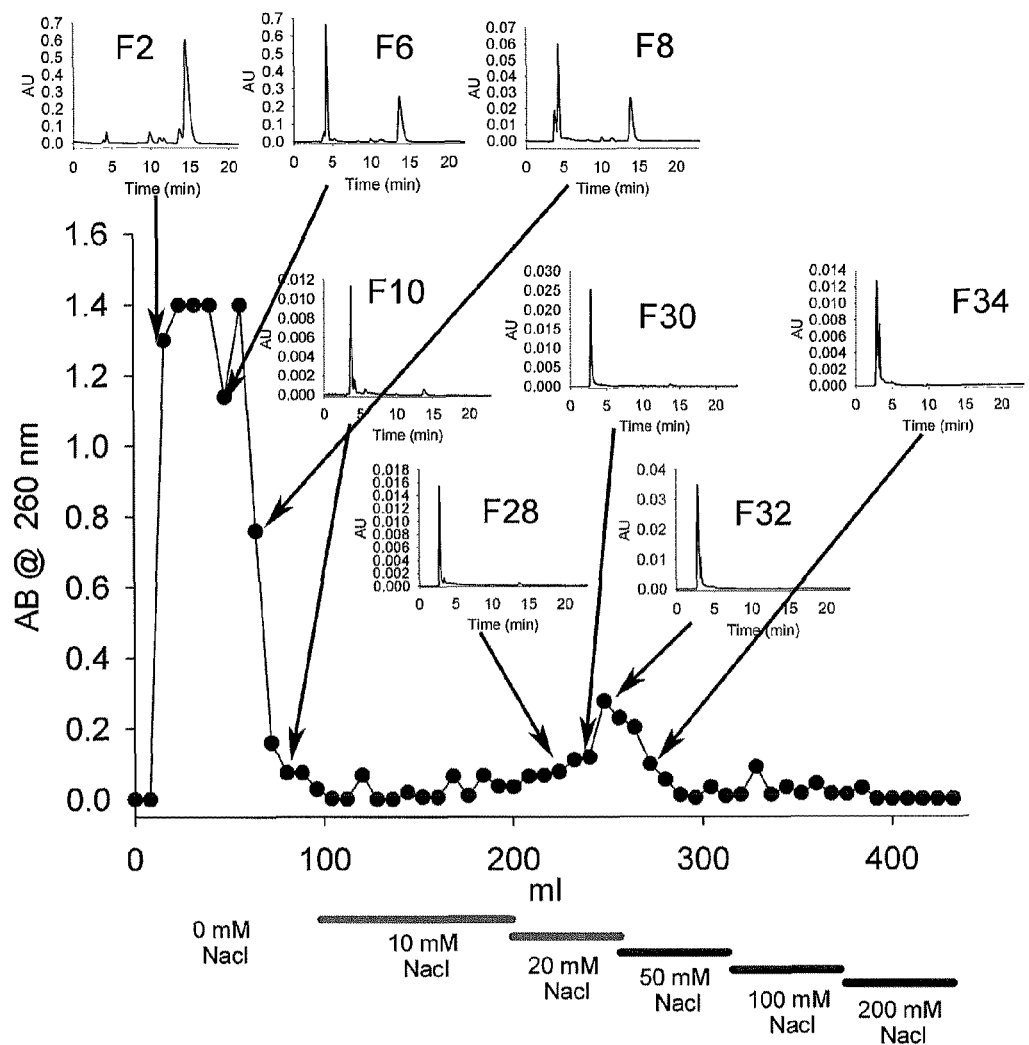
FIG. 1 shows the purification of NR from PAB076-conditioned media. Media collected from PAB076 grown to optical density at 600 nm ($OD_{600nm}$) of 60 in 2×YPD and supplemented with 5 mM NA was cleaned and concentrated by lyophilization followed by resuspension in cold methanol. This material was then loaded directly onto the SP-SEPHADEX resin.

NR is converted into NAD$^+$ through two distinct pathways. The first pathway utilizes the NR kinase, Nrk1, to produce nicotinamide mononucleotide, which is then converted into NAD$^+$. The second pathway cleaves NR into Nam and a ribose, by exploiting two independently acting enzymes uridine hydrolase 1 (Urh1) and purine nucleoside phosphorylase (Pnp1). Jointly these pathways are described as the NR salvage pathways and they feed into the NAD$^+$ cycle in two places.

It has now been shown that mutants which are deficient in NR salvage (i.e., nrk1 urh1 pnp1) can export NR in an Nrt-independent manner and support the growth of the NR auxotroph, qns1. More significantly, deletion of Nrt1 in a nrk1 urh1 pnp1 strain actually leads to increased extracellular NR accumulation. Moreover, NA or nicotinamide supplementation of a nrk1 urh1 pnp1 nrt1 strain increases NR yield from the strain. Accordingly, the present invention embraces a fungal strain deficient in the salvage and import of NR and use of said strain as a source for the production of NR. In addition, the invention provides a simple and scalable extraction method for inexpensively obtaining NR. Fungal strains of the present invention find application in large-scale production of NR as well as in the processes for fermenting of bread, soy, wine, beer, cider, kvass, root beer and other beverages, thereby providing added value of high nicotinamide riboside content. The nicotinamide riboside produced and isolated according to the present invention finds use in dietary supplement and pharmaceutical compositions for the prevention and treatment of a disease or condition associated with the nicotinamide riboside kinase pathway of NAD+ biosynthesis.

As indicated, the present invention embraces an isolated fungal strain deficient in nicotinamide riboside import and salvage. For the purposes of the present invention, a "fungal strain deficient in nicotinamide riboside import and salvage" is a strain that fails to import nicotinamide into the cytoplasm and also fails to utilize nicotinamide riboside as a NAD$^+$ precursor. In one embodiment, the fungal strain is produced by destroying or deleting by knocking out one or more genes involved in import and salvage of NR. Such gene deletions or disruptions are routinely practiced in the art and any conventional method, including those exemplified herein, can be employed.

In accordance with particular embodiments, the fungal strain of the invention does not express Nicotinamide Riboside Kinase 1 (Nrk1), Uridine Hydrolase 1 (Urh1), Purine Nucleoside Phosphorylase 1 (Pnp1), and Nicotinamide Riboside Transporter 1 (Nrt1). Genes encoding these proteins are known in the art and available from databases such as NCBI Entrez Nucleotide database, the *Saccharomyces* Genome Database, and the *Schizosaccharomyces pombe* genome project. For example, Nrk1 is provided under GENBANK accession nos. NP_014270 (SEQ ID NO:13, *S. cerevisiae*), NP_595603 (SEQ ID NO:14, *S. pombe*), XP_456163 (SEQ ID NO:15, *Kluveromyces lactis*), XP_001820220 (SEQ ID NO:16, *Aspergillus oryzae*), and XP_001386700 (SEQ ID NO:17, *Pichia stipitis*). Similarly, Urh1 is provided under GENBANK accession nos. NP_010688 (SEQ ID NO:18, *S. cerevisiae*), NP_593725 (SEQ ID NO:19, *S. pombe*), XP_452497 (SEQ ID NO:20, *K. lactis*), XP_001816861 (SEQ ID NO:21, *A. oryzae*), and XP_001384876 (SEQ ID NO:22, *P. stipitis*). Pnp1 is provided under GENBANK accession nos. NP_013310 (SEQ ID NO:23, *S. cerevisiae*), NP_593927 (SEQ ID NO:24, *S. pombe*), and XP_452943 (SEQ ID NO:25, *K. lactis*). In addition, Nrt1 is provided under GENBANK Accession Nos. NP_014714 (SEQ ID NO:26, *S. cerevisiae*), NP_595061 (SEQ ID NO:27, *S. pombe*), XP_453096 (SEQ ID NO:28, *K. lactis*), XP_001821563 (SEQ ID NO:29, *A. oryzae*), and XP_001383412 (SEQ ID NO:30, *P. stipitis*). Using these known sequences, the skilled artisan can readily disrupt or knockout the genes of interest to obtain a fungal strain deficient in NR transport and salvage. Strains with the desired gene knockouts or deletions can be identified by routine screens including, but not limited to, Southern blot analysis, RT-PCR, northern blot analysis, western blot analysis and the like.

In certain embodiments, the fungal strain of the present invention is used in the production of pharmaceuticals or in food fermentation, e.g., in the production of bread, wine, beer, cider, kvass, root beer, cheese, or soy sauce. In accordance with such embodiments, the fungal strain of the invention is selected from the genus *Saccharomyces, Schizosaccharomyces, Kluveromyces, Pichia,* or *Aspergillus* (e.g., *A. oryzae* or *A. sojae*). In particular embodiments, the fungal strain is a yeast, e.g., a fungus of the genus *Saccharomyces* (e.g., *S. cerevisiae, S. bayanus, S. boulardii, S. pastorianus, S. rouxii* and *S. uvarum*), *Schizosaccharomyces* (e.g., *S. pombe*), *Kluveromyces* (e.g., *K. lactis* and *K. fragilis*) and *Pichia*. In particular embodiments, the fungus is *Saccharomyces cerevisiae*.

Unexpectedly, by blocking NR uptake and salvage, the strain of this invention secretes at least 4.0 µM or 8 mg/L of nicotinamide riboside into the culture medium; a 40-fold increase over production of nicotinamide riboside in a wild-type strain. Furthermore, supplementation of the culture medium with either nicotinic acid or nicotinamide increases nicotinamide riboside production to as much as 7-8 µM, wherein even higher amounts of nicotinamide riboside are produced when the cells are cultured to extremely high densities. For example, S. cerevisiae grown to an $OD_{600nm}$ of 60 in 2×YPD+5 mM NA was capable of producing 28 µM nicotinamide riboside.

Thus, given the significant amount of nicotinamide riboside secreted by a fungal strain deficient in NR transport and salvage, the present also features a method for producing nicotinamide riboside by culturing the fungal strain of the invention in growth medium and recovering the methanol-solubilized nicotinamide riboside from the medium. In accordance with this method, the fungal strain is cultured in a fermentation, culture, or growth medium for production of nicotinamide riboside. An appropriate, or effective, culture medium refers to any medium in which a fungal strain of the present invention, when cultured, is capable of producing nicotinamide riboside. Such a medium is typically an aqueous medium composed of assimilable carbon, nitrogen and phosphate sources. Such a medium can also include appropriate salts, minerals, metals, and other nutrients. It should be recognized, however, that a variety of fermentation conditions are suitable and can be selected by those skilled in the art based upon art recognized culture conditions and the teachings of the present disclosure. In this regard, particular embodiments embrace the addition of nicotinamide or nicotinic acid to the culture medium. In other embodiments, the culture medium is formulated to support extremely high densities of cells, i.e., an $OD_{600\ nm}$ of at least 3.

Depending on the result to be achieved, the fungus can be cultured under anaerobic (deficient in oxygen) as well as aerobic (oxygenated) conditions. Under aerobic conditions, microorganisms such as yeast cells can break down sugars to end products such as $CO_2$ and $H_2O$. Under anaerobic conditions, yeast cells utilize an alternative pathway to produce $CO_2$ and ethanol. The fermentation reaction of the present invention is preferably anaerobic, i.e., partially or completely deficient in oxygen. Fermentation can also be used to refer to the bulk growth of microorganisms on a growth medium where no distinction is made between aerobic and anaerobic metabolism.

Fungal strains of the present invention can be cultured in conventional fermentation modes, which include, but are not limited to, batch, fed-batch, cell recycle, and continuous. In a fed-batch mode, when during fermentation some of the components of the medium are depleted, it may be possible to initiate the fermentation with relatively high concentrations of such components so that growth is supported for a period of time before additions are required. The preferred ranges of these components are maintained throughout the fermentation by making additions as levels are depleted by fermentation. Levels of components in the fermentation medium can be monitored by, for example, sampling the fermentation medium periodically and assaying for concentrations. Alternatively, once a standard fermentation procedure is developed, additions can be made at timed intervals corresponding to known levels at particular times throughout the fermentation. The additions to the fermentor may be made under the control of a computer in response to fermentor conditions or by a preprogrammed schedule. Moreover, to avoid introduction of foreign microorganisms into the fermentation medium, addition is performed using aseptic addition methods, as are known in the art. In addition, a small amount of anti-foaming agent may be added during the fermentation, or anti-foaming device may be employed.

In particular embodiments, recovery of the nicotinamide riboside from the culture medium is achieved by a simple, inexpensive process. The process involves solubilizing the nicotinamide riboside from the medium with methanol leaving behind a methanol-insoluble pellet; and subjecting the nicotinamide riboside to column chromatography to isolate the nicotinamide riboside from other contaminants. To facilitate the solubilization step, the culture medium can be concentrated, e.g., by lyophilization (freeze-drying) or roto-evaporation. In addition to the SP-SEPHADEX column chromatography exemplified herein, nicotinamide riboside can alternatively or also be purified by solid phase extraction, porous graphitic carbon or hydrophilic interaction chromatography. It is contemplated that the number and types of chromatographic columns employed will be dependent on the final use of the nicotinamide riboside and the level of purification desired.

In so far as yeast and other fungi are routinely used in the production of food products, the present invention also embraces a method for producing a nicotinamide riboside supplemented food product by providing a fermentable substrate and fermenting the fermentable substrate in the presence of the fungal strain of the invention. Food products, which can be produced in accordance with the method of this invention include, but are not limited to, bread, cheese, wine, beer, cider, kvass, root beer, or other beverages. As such, a fermentable substrate is intended to include any substratem which, when fermented, produces the above-referenced food products. Fermentable substrates include, but are not limited to, vegetables, oat, wheat, barley, millet, rice, rye, sorghum, potato, fruits, fruit juices, and the like.

Nicotinic acid is an effective agent in controlling low-density lipoprotein cholesterol, increasing high-density lipoprotein cholesterol, and reducing triglyceride and lipoprotein (a) levels in humans (see, e.g., Miller (2003) *Mayo Clin. Proc.* 78(6):735-42). Though nicotinic acid treatment effects all of the key lipids in the desirable direction and has been shown to reduce mortality in target populations, its use is limited because of a side effect of heat and redness termed flushing, which is significantly effected by the nature of formulation. Further, nicotinamide protects against stroke injury in model systems, due to multiple mechanisms including increasing mitochondrial NAD+ levels and inhibiting PARP (Klaidman, et al. (2003) *Pharmacology* 69(3):150-7). Altered levels of NAD+ precursors have been shown to effect the regulation of a number of genes and lifespan in yeast (Anderson, et al. (2003) *Nature* 423(6936):181-5).

NAD+ administration and NMN adenylyltransferase (Nmnat1) expression have also been shown to protect neurons from axonal degeneration (Araki, et al. (2004) *Science* 305:1010-1013). Because nicotinamide riboside is a soluble, transportable nucleoside precursor of NAD+, nicotinamide riboside can be used to protect against axonopathies such as those that occur in Alzheimer's Disease, Parkinson's Disease and Multiple Sclerosis. As such administration of nicotinamide riboside or a nicotinamide riboside supplemented-food product could also protect against axonal degeneration.

NMN adenylytransferase overexpression has been shown to protect neurons from the axonopathies that develop with ischemia and toxin exposure, including vincristine treatment (Araki, et al. (2004) *Science* 305:1010-1013). Vincristine is one of many chemotherapeutic agents whose use is limited by neurotoxicity. Thus, administration of nicotinamide riboside or a nicotinamide riboside supplemented-food product could be used to protect against neurotoxicity before, during or after cytotoxic chemotherapy.

Further, conversion of benign *Candida glabrata* to the adhesive, infective form is dependent upon the expression of EPA genes encoding adhesins whose expression is mediated by NAD+ limitation, which leads to defective Sir2-dependent silencing of these genes (Domergue, et al. (March 2005) *Science,* 10.1126/science.1108640). Treatment with nicotinic acid reduces expression of adhesins and increasing nicotinic acid in mouse chow reduces urinary tract infection by *Candida glabrata*. Thus, nicotinamide riboside or a nicotinamide riboside-supplemented food product can be used in the treatment of fungal infections, in particular, those of *Candida* species by preventing expression of adhesins.

Accordingly, the nicotinamide riboside or a nicotinamide riboside-supplemented food product of this invention could have therapeutic value in improving plasma lipid profiles, preventing stroke, providing neuroprotection with chemotherapy treatment, treating fungal infections, preventing or reducing neurodegeneration, or in prolonging health and well-being. Thus, the present invention is further a method for preventing or treating a disease or condition associated with the nicotinamide riboside kinase pathway of NAD+biosynthesis by administering an effective amount of a nicotinamide riboside composition. Diseases or conditions which typically have altered levels of NAD+ or NAD+ precursors or could benefit from increased NAD+biosynthesis by treatment with nicotinamide riboside include, but are not limited to, lipid disorders (e.g., dyslipidemia, hypercholesterolaemia or hyperlipidemia), stroke, neurodegenerative diseases (e.g., Alzheimer's, Parkinsons and Multiple Sclerosis), neurotoxicity as observed with chemotherapies, *Candida glabrata* infection, and the general health declines associated with aging. Such diseases and conditions can be prevented or treated by diet supplementation or providing a therapeutic treatment regime with a nicotinamide riboside composition.

An effective amount of nicotinamide riboside is one which prevents, reduces, alleviates or eliminates the signs or symptoms of the disease or condition being prevented or treated and will vary with the disease or condition. Such signs or symptoms can be evaluated by the skilled clinician before and after treatment with the nicotinamide riboside to evaluate the effectiveness of the treatment regime and dosages can be adjusted accordingly.

The nicotinamide riboside produced in accordance with the method of the invention can be conveniently used or administered in a composition containing the active agent in combination with a pharmaceutically acceptable carrier. Such compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A carrier, pharmaceutically acceptable carrier, or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Nicotinamide riboside produced in accordance with the method of the invention can be administered via any route include, but not limited to, oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration, administration to the liver by intraportal delivery, as well as direct organ injection (e.g., into the liver, into the brain for delivery to the central nervous system). The most suitable route in any given case will depend on the nature and severity of the condition being treated and on the nature of the particular compound which is being used.

A physician or veterinarian having ordinary skill in the art can readily determine and prescribe the effective amount of the pharmaceutical composition required for prevention or treatment in an animal subject such as a human, agriculturally-important animal, pet or zoological animal.

In addition to the specific fungal strains disclosed herein, it is expected that these fungal strains may be further manipulated to achieve other desirable characteristics, or even higher specific yields of fermentation products. For example, selection of strains by passaging the strains of the present invention on medium containing a particular substrate of interest may result in improved fungi with enhanced fermentation rates.

The invention is described in greater detail by the following non-limiting examples.

Example 1

Materials and Methods

Yeast Strains and Medium. All *Saccharomyces cerevisiae* strains used in this study were derivatives of the common wild-type strain, BY4742. Construction of single deletion strains was according to established methods (Winzeler, et al. (1999) *Science* 285:901-6). Additional deletions were created by direct transformation with PCR products (Brachmann, et al. (1998) *Yeast* 14:115-32). Primers employed in the PCR reactions are listed in Table 1.

TABLE 1

| Primer | Sequence (5' to 3') | SEQ ID NO: |
|---|---|---|
| 14050 | gctctagaCAGACAAGTGGTATGCATATCC | 1 |
| 14051 | cggggtaccGATGTGCTGTGACTGGG | 2 |
| 14060 | gccgctcgagCTTCCCGCTATGTAATAAATAGAGG | 3 |
| 14061 | cgcggatccGCATCATCTGTCAATTTCCTTG | 4 |
| 14121 NRT1 Deletion F | GAATTTATATTATTCTTTATTGTACTGATATCCCCATTATAACTATCAAAAAAAGGACTTCAGCACCTGTGCGGTATTTCACACCG | 5 |
| 14122 NRT1 Deletion R | CTGTACAGATTTTCAAATGAAGCGTTGAAGTTTCCTCTTTGTATATTTGAGATCTTCATTTTATCAGATTGTACTGAGAGTGCA | 6 |
| 14124 NRT1 Diagnostic F | CTAGTGTTGCTACCGCTATTTGTTCTTCG | 7 |
| 14124 NRT1 Diagnostic R | GCAGTCGAGGATCGATCTGGTAGTATTC | 8 |
| 4750 | AATAGCGTGCAAAAGCTATCGAAGTGTGAGCTAGAGTAGAACCTCAAAATAGATTGTACTGAGAGTGCA | 9 |
| 4751 | CTAATCCTTACAAAGCTTTAGAATCTCTTGGCACACCCAGCTTAAAGGTCTGTGCGGTATTTCACACCG | 10 |

TABLE 1-continued

| Primer | Sequence (5' to 3') | SEQ ID NO: |
|---|---|---|
| 14113 | CTCTCCGAGCTCGGATTCTTTGTCATCAGACAACTTGTTGAGTGG | 11 |
| 14112 | GTGCCCAAGCTTGTGTGCCAATGTAGCGTGGTTGCATG | 12 | pPAB01 was constructed by amplifying the PNP1 gene from wild-type yeast genomic DNA with primers 14061 and 14060. The PCR product was inserted into pRS416 with XhoI and BamHI. pPAB02 was constructed by amplifying the URH1 gene using primers 14051 and 14050. The PCR product was inserted into pRS416 with KpnI and XbaI. Plasmids were confirmed by DNA sequencing and used for construction of deletion strains.

A yeast strain carrying disruption of the NRK1 locus was made by transformation of the strain BY165-1d with the HIS3 marker introduced into disruption cassette by PCR with primers 4750 and 4751.

Plasmid pNRT1, carrying NRT1 under the control of its own promoter, was created by amplifying the gene from BY4742 DNA using primers 14112 and 14113. After digestion with SacI and HindIII, the product was inserted into pRS317.

Strains generated and used herein are listed in Table 2.

TABLE 2

| Name | Genotype |
|---|---|
| B4742[a] | MATα his3Δ1 leu2Δ0 lys2Δ0 ura3Δ0 |
| PAB011 | BY4742 nrt1Δ::kanMX4 |
| PAB038 | BY4742 pnp1Δ::kanMX4 urh1::NAT nrk1Δ::HIS3 |
| PAB075 | BY4742 nrt1Δ::kanMX4 fun26Δ::URA3 |
| PAB076 | BY4742 pnp1Δ::kanMX4 urh1::NAT nrk1Δ::HIS3 nrt1Δ::URA3 |
| PY165-d | qns1::URA3 pB175 |

[a]Brachmann, et al. (1998) Yeast 14: 115-32.

NA-free synthetic dextrose complete media (SDC) and its vitamin supplemented forms are described in the art (Wickerham (1946) *J. Bacteriol.* 52:293-301). 2×SDC and 2×YPD were prepared as the more concentrated forms of the conventional preparation.

qns1 Bioassay. Strain BY165-1d, the chromosomal deletion of qns1 carrying the QNS1 plasmid pB175 (Bieganowski, et al. (2003) *J. Biol. Chem.* 278:33049-33055), was plated on 5-FOA plates supplemented with NR to remove pB175. The resulting strain was cultured on NR containing media at all times. Conditioned media was prepared by incubating the specified yeast strain in the appropriate media. After 18 hours the cells were removed by centrifugation followed by filtration. The conditioned media was retained and mixed in a 1 to 1 ratio with fresh 2×SDC. BY165-1d with no pB175 was incubated in the resulting media and growth was measured spectroscopically.

MALDI-MS NR Quantification. NR content in conditioned media was measured using MALDI-MS. Prior to measurement, [$^{18}$O] NR was added to the media to a final concentration of 10 μM as an internal standard. One microliter of the [$^{18}$O] spiked samples was mixed with 1 μl 2,5-Dihydroxy benzoic acid (DHB) matrix, and the mixture was allowed to air dry. The DHB matrix was composed of 50% acetonitrile saturated with DHB. MS spectra were collected on the ABI Voyager-DE Pro MALDI-TOF mass spectrometer and the ratio of the labeled standard to the unlabeled NR was used to determine the NR concentration.

HPLC Measurements. NA, Nam and NR were also measured using HPLC. Media samples were injected directly onto a Princeton SPHER-60 SAX 60A u (250×4.6 mm) column and separated by an isocratic run of 20 mM $KH_2PO_4$. Metabolites were detected spectroscopically at 260 nm and quantified by comparison to a standard curve.

NR Extraction. NR was extracted from 2×YPD. PAB076 was incubated in 500 ml of 2×YPD to an $OD_{600nm}$ of 60 (~60 hours). The media was divided into 150 ml portions and frozen at −80° C. As the first step in the purification process, the samples were lyophilized and resuspended in 25 ml of cold methanol. Cold methanol solubilized the NR but left the majority of the contaminants as a pellet after centrifugation. The methanol samples were then lyophilized again and resuspended in 5 ml of water. The aqueous samples were then run over a 10 ml SP-SEPHADEX column, and eluted using a stepped NaCl gradient. NR eluted at 25-50 mM NaCl. Fractions were analyzed using HPLC, and NR was confirmed using MALDI-MS and a biological $NAD^+$ assay.

Biological $NAD^+$ Assay. Yeast cultures were grown with agitation in 0.5 L cultures. During growth, the $OD_{600\,nm}$ of 1:10 diluted cells were recorded and 20 ml cultural volumes were pelleted, washed with water, repelleted, and frozen at −80° C. Cell pellets were extracted in 250 ml of ice-cold 1 M formic acid saturated with butanol. After 30 minutes, 62.5 ml of 100% (w/v) trichloroacetic acid was added to each extract, and the samples were allowed to precipitate on ice for 15 minutes. Samples were microcentrifuged for 5 minutes, and the acid soluble supernatants were recovered. Pellets were washed with 125 ml of 20% TCA and repelleted. First and second supernatants were pooled and measured volumetrically. In three 1 ml cuvettes, reactions were assembled containing 10 ml 5 mg/ml alcohol dehydrogenase (two samples) or 10 ml water (control sample), and this was followed by addition of 840 ml 360 mM Tris (pH 9.7), 240 mM lysine, 0.24% (v/v) EtOH, and 150 ml extract. After a 5 minute incubation at room temperature, the spectrophotometer was zeroed against the control sample for determining the alcohol dehydrogenase-dependent increase in absorbance at 340 nm of the duplicate reactions. Mean net absorbances were converted to molar $NAD^+$ with the extinction coefficient of NADH ($6220 M^{-1} \cdot cm^{-1}$). Molar $NAD^+$ in the cuvette was converted to molar $NAD^+$ in the extract by a factor of 6.67. Moles of $NAD^+$ in the extract were determined from the fraction of the extract assayed. To determine the intracellular volumes corresponding to the extracts and the corresponding intracellular NAD+concentrations, a nonlinear conversion between the 1:10 diluted $OD_{600\,nm}$ values and the cell number was used (Burke, et al. (2000) *Methods in Yeast Genetics*, Cold Spring Harbor, N.Y.: Cold Spring Harbor Press) and took the volume of a haploid cell to be $7 \times 10^{-14}$ (Sherman (1991) *Methods Enzymol.* 194:3-21). For cells grown in media containing nicotinic acid, $NAD^+$ concentrations were determined, in duplicate, 6 to 18 times during the growth of a liquid culture. For cells grown in media without nicotinic acid, the cells were taken with 1:10 diluted $OD_{600\,nm}$ values of 0.095-0.105, and the $NAD^+$ concentrations were determined, in duplicate, from three to eight independent cultures.

Example 2

NR Export is Nrt1-Independent

In yeast, NR has activity as a qns1-bypassing and lifespan extending vitamin. It has also been found that NR is an intracellular and extracellular metabolite. On the basis of the discovery of the specific NR transporter, Nrt1 (YOR071C gene), it was of interest to determine whether this importer is responsible for the observed NR export activity.

The NR-non-salvaging genotype nrk1 urh1 pnp1 (strain PAB038) exhibits reduced $NAD^+$ levels and exports NR. To test whether Nrt1 is required for the export of NR, NRT1 was deleted in the PAB038 strain through homologous recombination using the URA3 marker to replace NRT1.

Extracellular NR is detectable using a qns1 bioassay that relies on the NR auxotrophy of the qns1 strain. In this assay, the strains being tested for NR export are grown overnight in SDC medium, at which point the cells are removed and the conditioned media is retained. The qns1 strain is then incubated in medium containing equal measures of conditioned media and fresh 2×SDC. In this assay, the extent of qns1 growth is proportional to the extracellular concentration of NR. Based on qns1 growth, the nrt1 deletion does not reduce extracellular NR. On the contrary NR levels are actually elevated. By comparison to SDC supplemented with purified NR, it was estimated that the NR-non-salvaging strain, PAB038, produced 1 μM extracellular NR when incubated to an OD of 3, whereas the NR-non-salvaging and NR-non-importing strain, nrk1 urh1 pnp1 nrt1 (PAB076), produced 2 μM extracellular NR under the same growth conditions. The excess of extracellular NR in the nrt1 mutant was apparently due to the fact that NR export was Nrt1-independent. The results of this analysis indicated that in strain PAB076, NR can be exported but not reabsorbed, resulting in higher accumulation of extracellular NR by the PAB076 strain.

Example 3

Increases in NR Yield

NR has potential to become an important vitamin for daily dietary supplementation and at higher levels a drug for the treatment of disorders like dyslipidemia. One of the hurdles to the development of NR as a product for human consumption has been the difficulty and expense of enzymatic or chemical synthesis. Nicotinamide riboside is costly to produce, largely because of the cost of blocked (i.e., acetylated or benzoylated) ribose used in its organic synthesis (Tanimori, et al. (2002) *Bioorg. Med. Chem.* 12:1135-1137). As such, improved NR export from yeast may provide a clean and simple biological alternative to the current modes of NR production. It was contemplate that one possible way to upregulate NR export would be to supplement yeast with the inexpensive $NAD^+$ precursors NA or Nam. Niacin supplementation would have two potentially beneficial effects: first it would help replenish $NAD^+$ lost in the synthesis of NR and second it would lead to the over expression of NR producing 5' nucleotidases.

Assaying the content of NR in media conditioned by PAB076 in the presence of 1 mM NA or Nam revealed that supplementation substantially increased the amount of NR produced as assayed by qns1 growth. The extent of qns1 growth was higher than the growth provide by 3 μM NR, indicating that the concentration of NR in the conditioned media was at least 6 μM.

The qns1 bioassay is an effective method of detecting the presence of low amounts of NR in conditioned media but becomes nonlinear at high concentrations. To more accurately measure the extracellular concentration of NR, MALDI-MS was employed with an internal standard of [$^{18}O$] NR at a concentration of 10 μM. The concentration of NR in the media was determined from the ratio of the labeled standard to the unlabeled NR.

Using MS quantification, it was found that wild-type yeast had 0.120±0.4 μM NR, PAB038 (pnp1 urh1 nrk1) had 1.2 μM±0.4 μM NR and PAB076 (pnp1 urh1 nrk1 nrt1) had 4.0±0.9 μM NR, in conditioned medium from cells grown in SDC to an OD of 3 (Table 3). Adding 1 mM NA, increased the extracellular NR produced by both PAB076 and PAB038 to a concentration of 7.7±1.1 µM and 3.9±1.5 µM respectively. Changing the niacin to Nam or supplementing with both niacins did not further improve the NR yield from the PAB076.

TABLE 3

| Strain and Condition | [NR] µM |
| --- | --- |
| Wild-type SDC (OD 3) | 0.12 ± 0.4 |
| PAB038 SDC (OD 3) | 1.20 ± 0.4 |
| PAB038 SDC + 1 mM NA (OD 3) | 3.90 ± 1.5 |
| PAB076 SDC (OD 3) | 4.06 ± 0.9 |
| PAB076 SDC + 1 mM NA (OD 3) | 7.70 ± 1.1 |
| PAB076 SDC + 1 mM Nam (OD 3) | 7.17 ± 0.2 |
| PAB076 SDC + 1 mM Nam & NA (OD 3) | 7.30 ± 0.3 |
| PAB076 YPD + 1 mM NA (OD 15) | 10.60 ± 5.6 |
| PAB076 2X YPD + 1 mM NA (OD 21) | 21.20 ± 4.6 |
| PAB076 SDC + 5 mM NA (OD 7) | 16.80 ± 0.3 |
| PAB076 2X SDC + 5 mM NA (OD 13) | 20.80 ± 4.2 |
| PAB076 2X YPD + 5 mM NA (OD 60) | 28.15 ± 8.5 |

By adding NA or Nam, the amount of extracellular NR produced could be doubled. To further increase the yield, cells were cultured to extremely high densities. PAB076 was incubated in YPD, 2×YPD, SDC or 2×SDC and growth was measured over a period of 31 hours. Surprisingly, PAB076 was able to grow to an unusually high density in all three media formulations (Table 4). For example, this strain attained an OD of 29 when grown in YPD and an OD of 35 when grown in 2×YPD. To determine the genetic cause of this phenotype, the growth of other related strains was assayed (Table 4). Only one other strain, nrt1 fun26 (PAB75), had this unusual ability to grow to high cell density. The common element present in these two strains and absent in the others was an intact URA3 gene. URA3 was used to knock out nrt1 in the PAB076 stain and fun26 in PAB075. Other nonrelated strains chosen from lab stocks also had the same URA3-dependent high growth phenotype.

TABLE 4

| Strain and Condition | OD at 31 hours |
| --- | --- |
| nrk1 urh1 pnp1 nrt1 URA3 2X YPD | 35.0 |
| nrk1 urh1 pnp1 nrt1 URA3 YPD | 29.0 |
| nrk1 urh1 pnp1 nrt1 URA3 SDC | 7.0 |
| nrk1 urh1 pnp1 ura3 2X YPD | 12.9 |
| nrk1 urh1 pnp1 ura3 YPD | 8.1 |
| nrk1 urh1 pnp1 ura3 SDC | 6.4 |
| Wild-type (ura3) 2X YPD | 12.2 |
| Wild-type (ura3) SDC | 5.5 |
| nrt1 ura3 2X YPD | 13.0 |
| nrt fun26 URA3 2X YPD | 33.7 |
| nrt fun26 URA3 2X YPD | 33.2 |
| nrk1 urh1 pnp1 nrt1 URA3 2X YPD | 36.1 |

Growing cells to extremely high cultural density dramatically increased extracellular NR accumulation (Table 3). Cells incubated in 2×SDC (5 mM NA) to an OD of 13 and cells incubated in 2×YPD (5 mM NA) to an OD of 60 produced the highest amounts of extracellular NR, 20.2±4.3 µM and 28.1±8 µM extracellular NR, respectively. Cells that were incubated in 2×YPD, but did not reach stationary phase produced somewhat less extracellular NR than cells grown to an OD of 60. Similarly, cells incubated in 1×SDC or 1×YPD produced significantly less NR than the cells incubated in the 2× formulations. From this data, it appears that the final concentration of NR is both a function final cell number and whether or not the culture reached stationary.

Example 4

Purification of NR from PAB076-Conditioned Media

Cultures of PAB076 (500 mL) were grown in 2×SDC or 2×YPD with 5 mM NA, to an OD of 13 and 60, respectively. To extract NR from this medium, a two step process was implemented that first concentrated NR by lyophilization and methanol extraction, and then separated NR from contaminants using SP-SEPHADEX chromatography. The SP-SEPHADEX fractions were analyzed by HPLC. NA and the majority of the media components eluted in the first 100 ml of the run that contained no salt (FIG. 1). NR was retained by the resin and eluted between 20 and 50 mM NaCl in fractions 27-36. The majority of these fractions were more than 98% pure NR, although the early fractions contained trace amounts of NA. Each fraction was concentrated by lyophilization and the concentration of NR was determined by absorbance at 259 nm. The total yield was ~700 µg of NR from 150 ml of the media or 5.6 mg/L. Based on MALDI-MS measurements, the concentration of NR in the conditioned 2×YPD prior to extraction was ~8 mg/L. It was found that NR from fraction 28 and from pooled fractions 31-34 (added at 10 µM) was capable of increasing intracellular $NAD^+$ in wild-type yeast as efficiently as chemically or enzymatically synthesized NR.

In so far as 2×SDC media could not be effectively fractionated by SP-SEPHADEX because of the high salt content of this media, conditioned 2×SDC medium would require desalting (e.g., with a disposable C18 spin columns) prior to chromatography.

In addition to the above-described approaches, other improvements are contemplated for increasing the yield of NR. These include the use of a chemostat fermenter and the use of industrial scale preparative HPLC chromatography; and genetically engineering a PAB076 strain that also overexpresses the major NMN 5' nucleotidase thereby increasing extracellular NR production and lowering the concentration of NA supplementation. The recommended daily allowance of niacin is 15 mg, and with only slight improvements made possible by industrialization, one liter or less of yeast would be able to produce the daily Niacin requirement in the form of NR.

What is claimed is:

1. An isolated *Saccharomyces* strain deficient in the expression of genes involved in nicotinamide riboside import and salvage.

2. The *Saccharomyces* strain of claim 1, wherein said strain does not express Nicotinamide Riboside Kinase 1 (Nrk1), Uridine Hydrolase 1 (Urh1), Purine Nucleoside Phosphorylase (Pnp1), and Nicotinamide Riboside Transporter 1 (Nrt1).

3. The *Saccharomyces* strain of claim 1, wherein said strain secretes at least 8 mg/L nicotinamide riboside.

4. The *Saccharomyces* strain of claim 1, wherein said fungus is *Saccharomyces cerevisiae*.

5. A method for producing nicotinamide riboside comprising culturing the *Saccharomyces* strain of claim 1 in culture medium and recovering nicotinamide riboside from the medium thereby producing nicotinamide riboside.

6. The method of claim 5, wherein the culture medium comprises nicotinic acid or nicotinamide.

7. The method of claim 5, wherein the fungal strain is cultured to an optical density of at least 3.

8. The method of claim 5, wherein the nicotinamide riboside is recovered by solubilizing nicotinamide riboside from the medium with methanol and subjecting the nicotinamide riboside to column chromatography.

9. A method for producing a nicotinamide riboside-supplemented food product comprising providing a fermentable substrate and fermenting the fermentable substrate in the presence of the *Saccharomyces* strain of claim 1 thereby producing a nicotinamide riboside supplemented food product.

10. A nicotinamide riboside supplemented food product fermented in the presence of the *Saccharomyces* strain of claim 1.

11. The product of claim 10, wherein said food product is wine, beer, cider, kvass, root beer, soy sauce or bread.

* * * * *

SEQUENCE LISTING

<160> NUMBER OF SEQ ID NOS: 30

<210> SEQ ID NO 1
<211> LENGTH: 30
<212> TYPE: DNA
<213> ORGANISM: Artificial sequence
<220> FEATURE:
<223> OTHER INFORMATION: Synthetic oligonucleotide -continued

<400> SEQUENCE: 1
gctctagaca gacaagtggt atgcatatcc                                              30

<210> SEQ ID NO 2
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 2
cggggtaccg atgtgctgtg actggg                                                  26

<210> SEQ ID NO 3
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 3
gccgctcgag cttcccgcta tgtaataaat agagg                                        35

<210> SEQ ID NO 4
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 4
cgcggatccg catcatctgt caatttcctt g                                            31

<210> SEQ ID NO 5
<211> LENGTH: 86
<212> TYPE: DNA
<213> ORGANISM: Artificial sequence
<220> FEATURE:
<223> OTHER INFORMATION: Synthetic oligonucleotide

<400> SEQUENCE: 5
gaatttatat tattctttat tgtactgata tccccattat aactatcaaa aaaggactt              60 cagcacctgt gcggtatttc acaccg                                                  86

<210> SEQ ID NO 6
<211> LENGTH: 84
<212> TYPE: DNA
<213> ORGANISM: Artificial sequence
<220> FEATURE:
<223> OTHER INFORMATION: Synthetic oligonucleotide

<400> SEQUENCE: 6
ctgtacagat tttcaaatga agcgttgaag tttcctcttt gtatatttga gatcttcatt             60
ttatcagatt gtactgagag tgca                                                    84

<210> SEQ ID NO 7
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 7
ctagtgttgc taccgctatt tgttcttcg                                               29

-continued

<210> SEQ ID NO 8
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 8
gcagtcgagg atcgatctgg tagtattc                                      28

<210> SEQ ID NO 9
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 9
aatagcgtgc aaaagctatc gaagtgtgag ctagagtaga acctcaaaat agattgtact    60
gagagtgca                                                           69

<210> SEQ ID NO 10
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 10
ctaatcctta caaagcttta gaatctcttg gcacacccag cttaaaggtc tgtgcggtat    60
ttcacaccg                                                           69

<210> SEQ ID NO 11
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 11
ctctccgagc tcggattctt tgtcatcaga caacttgttg agtgg                   45

<210> SEQ ID NO 12
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 12
gtgcccaagc ttgtgtgcca atgtagcgtg gttgcatg                           38

<210> SEQ ID NO 13
<211> LENGTH: 240
<212> TYPE: PRT
<213> ORGANISM: Saccharomyces cerevisiae

<400> SEQUENCE: 13

Met Thr Ser Lys Lys Val Ile Leu Val Ala Leu Ser Gly Cys Ser Ser
1               5                   10                  15

Ser Gly Lys Thr Thr Ile Ala Lys Leu Thr Ala Ser Leu Phe Thr Lys
            20                  25                  30

Ala Thr Leu Ile His Glu Asp Asp Phe Tyr Lys His Asp Asn Glu Val
        35                  40                  45

```
Pro Val Asp Ala Lys Tyr Asn Ile Gln Asn Trp Asp Ser Pro Glu Ala
     50                  55                  60

Leu Asp Phe Lys Leu Phe Gly Lys Glu Leu Asp Val Ile Lys Gln Thr
 65                  70                  75                  80

Gly Lys Ile Ala Thr Lys Leu Ile His Asn Asn Val Asp Asp Pro
                 85                  90                  95

Phe Thr Lys Phe His Ile Asp Arg Gln Val Trp Asp Glu Leu Lys Ala
             100                 105                 110

Lys Tyr Asp Ser Ile Asn Asp Lys Tyr Glu Val Ile Val Asp
         115                 120                 125

Gly Phe Met Ile Phe Asn Asn Thr Gly Ile Ser Lys Lys Phe Asp Leu
130                 135                 140

Lys Ile Leu Val Arg Ala Pro Tyr Glu Val Leu Lys Lys Arg Arg Ala
145                 150                 155                 160

Ser Arg Lys Gly Tyr Gln Thr Leu Asp Ser Phe Trp Val Asp Pro Pro
                 165                 170                 175

Tyr Tyr Phe Asp Glu Phe Val Tyr Glu Ser Tyr Arg Ala Asn His Ala
             180                 185                 190

Gln Leu Phe Val Asn Gly Asp Val Glu Gly Leu Leu Asp Pro Arg Lys
         195                 200                 205

Ser Lys Asn Ile Lys Glu Phe Ile Asn Asp Asp Thr Pro Ile Ala
210                 215                 220

Lys Pro Leu Ser Trp Val Cys Gln Glu Ile Leu Lys Leu Cys Lys Asp
225                 230                 235                 240

<210> SEQ ID NO 14
<211> LENGTH: 230
<212> TYPE: PRT
<213> ORGANISM: Schizosaccharomyces pombe

<400> SEQUENCE: 14

Met Thr Arg Lys Thr Ile Ile Val Gly Val Ser Gly Ala Ser Cys Ser
 1               5                  10                  15

Gly Lys Ser Thr Leu Cys Gln Leu Leu His Ala Ile Phe Glu Gly Ser
                 20                  25                  30

Ser Leu Val His Glu Asp Asp Phe Tyr Lys Thr Asp Ala Glu Ile Pro
             35                  40                  45

Val Lys Asn Gly Ile Ala Asp Trp Asp Cys Gln Glu Ser Leu Asn Leu
 50                  55                  60

Asp Ala Phe Leu Glu Asn Leu His Tyr Ile Arg Asp His Gly Val Leu
 65                  70                  75                  80

Pro Thr His Leu Arg Asn Arg Glu Asn Lys Asn Val Ala Pro Glu Ala
                 85                  90                  95

Leu Ile Glu Tyr Ala Asp Ile Ile Lys Glu Phe Lys Ala Pro Ala Ile
             100                 105                 110

Pro Thr Leu Glu Gln His Leu Val Phe Val Asp Gly Phe Met Met Tyr
         115                 120                 125

Val Asn Glu Asp Leu Ile Asn Ala Phe Asp Ile Arg Leu Met Leu Val
130                 135                 140

Thr Asp Phe Asp Thr Leu Lys Arg Arg Arg Glu Ala Arg Thr Gly Tyr
145                 150                 155                 160

Ile Thr Leu Glu Gly Phe Trp Gln Asp Pro Pro His Tyr Phe Glu Asn
                 165                 170                 175

Tyr Val Trp Pro Gly Tyr Val His Gly His Ser His Leu Phe Val Asn
             180                 185                 190
```

```
Gly Asp Val Thr Gly Lys Leu Leu Asp Lys Arg Ile Gln Leu Ser Pro
            195                 200                 205

Ser Ser Lys Met Ser Val Arg Asp Asn Val Gln Trp Ala Ile Asn Ser
210                 215                 220

Ile Leu Asn Ala Leu Gln
225                 230

<210> SEQ ID NO 15
<211> LENGTH: 242
<212> TYPE: PRT
<213> ORGANISM: Kluyveromyces lactis

<400> SEQUENCE: 15

Met Thr Ser Ser Lys Leu Val Leu Ile Ala Ile Ser Gly Cys Ser Ser
1               5                   10                  15

Ser Gly Lys Thr Thr Leu Thr Lys Leu Thr Ser Asn Ala Ile Pro Arg
            20                  25                  30

Ser Ser Val Leu His Glu Asp Asp Phe Tyr Lys Pro Asp Ala Gln Ile
        35                  40                  45

Pro Leu Asn Glu Lys Tyr Gln Ile Ala Asp Trp Asp Cys Pro Glu Ala
50                  55                  60

Leu Asp Ile Pro Ala Phe Lys Arg Glu Leu Asp Gln Ile Lys Glu Thr
65                  70                  75                  80

Gly Leu Ile Lys Ser Lys Leu Ile His Asn Asp Asn Val Asp Asp Ile
                85                  90                  95

Thr Lys Phe Asp Ile Ser Pro Glu Asp Trp Asp Ser Leu Lys Arg Lys
            100                 105                 110

Tyr Ala Ile Val Gln Asn Ser Asp Leu Lys Ile Val Leu Val Asp Gly
        115                 120                 125

Phe Met Ile Phe Asn Asp Glu Glu Leu Thr Lys Lys Phe Asp Ile Lys
130                 135                 140

Ile Phe Val Arg Ala Pro Tyr Glu Val Leu Lys Lys Arg Arg Asn Ala
145                 150                 155                 160

Arg Ala Gly Tyr Lys Thr Ile Asp Ser Tyr Trp Val Asp Pro Pro Tyr
                165                 170                 175

Tyr Phe Asp Glu Phe Val Tyr Lys Ser Tyr Arg Asn Glu His Lys Tyr
            180                 185                 190

Met Phe Glu Asp Glu Asp Ile Glu Gly Gln Leu Lys Arg Asn Thr Gly
        195                 200                 205

Leu Phe Glu Leu Lys Asn Asp Asp Ile Asn Ile Ser Asp Ala Leu
210                 215                 220

Asn Ala Ile Ala Asp His Ile Val Glu Thr Leu Asn Ala Ser Ser Leu
225                 230                 235                 240

Leu Glu

<210> SEQ ID NO 16
<211> LENGTH: 315
<212> TYPE: PRT
<213> ORGANISM: Aspergillus oryzae

<400> SEQUENCE: 16

Met Ala Ser Gln Thr Gly Val Ile Gly Ile Ser Gly Pro Ser Ser Ser
1               5                   10                  15

Gly Lys Thr Thr Leu Ala Arg Leu Leu Gln Arg Ile Phe Ser Lys Ala
            20                  25                  30

Asp Glu Ser Leu Phe Thr Phe Ile Val His Glu Asp Asp Phe Tyr Phe
```

```
                35                  40                  45
Pro Asp Asp Arg Ile Pro Tyr Thr Thr Thr Ala Ser Gly Lys Thr Val
 50                  55                  60

Gln Asp Trp Asp Thr Ile Asp Ala Ile Asp Val Lys Phe Leu Ser Ser
 65                  70                  75                  80

Ala Leu Ser Tyr Ile Arg Asp His Gly Gln Leu Pro Pro Arg Leu Lys
                 85                  90                  95

Ser Ile Gln Asp Leu Asn Glu Lys Ser Asp Ser Gly Val Asp Glu Gly
            100                 105                 110

Thr Ile Leu Gln Leu Gln Gln Glu Val Gly Gly Arg Leu Arg Ala Arg
        115                 120                 125

Ala Pro Ala Lys Arg Thr Ile Ala Phe Leu Glu Gly Phe Leu Leu Tyr
130                 135                 140

Ser Pro Pro Glu Ser Glu Asp Lys Asp His Val Leu Arg Ser Val His
145                 150                 155                 160

Lys Asn Ile Asp Val His Leu Phe Leu Pro Ala Pro Tyr Asp Met Val
                165                 170                 175

Lys Ser Arg Arg Glu Gly Arg Ser Gly Tyr Val Thr Ser Gly Pro Ala
            180                 185                 190

Pro Glu Pro Thr Ser Leu Pro Gln Arg Ser Ser Val Ser Asp Glu Val
        195                 200                 205

Asp Leu Glu Gly Glu Asp Asp Arg Pro Pro Gln Asn Phe Trp Thr Asp
    210                 215                 220

Pro Pro Gly Tyr Val Asp Asp Ile Val Trp Pro Arg Tyr Val Gln Asp
225                 230                 235                 240

His Ala Trp Leu Ile Leu Pro Glu Gly Glu Ser Gln Lys Ser Asn Thr
                245                 250                 255

Leu Ser Ala Asp Ser Gln Glu Leu Val Asn Lys Val Gly Gln Gly Val
            260                 265                 270

Asn Leu Arg Thr Asn Ala Gly Val Ile Ala Pro Gly Glu Gly Thr
        275                 280                 285

Lys Pro Met Val Asp Ile Leu Lys Trp Ala Val Glu Glu Val Leu Lys
    290                 295                 300

Tyr Leu Glu Arg Asn Ile Leu Glu Val His Glu
305                 310                 315

<210> SEQ ID NO 17
<211> LENGTH: 244
<212> TYPE: PRT
<213> ORGANISM: Pichia stipitis

<400> SEQUENCE: 17

Met Thr His Glu Glu Tyr Lys Gln Val Val Ile Ala Phe Gly Gly
 1               5                  10                  15

Pro Ser Ser Ser Gly Lys Thr Thr Cys Ala Lys Ala Val His Ser Leu
                20                  25                  30

Ile Lys Asn Ser Arg Leu Ile His Leu Asp Asp Phe Tyr Leu Ala Asp
            35                  40                  45

His Leu Ile Pro Val Asp Pro Val Thr Gly Gln Gln Asn Trp Asp Val
        50                  55                  60

Pro Glu Ala Leu Asp Phe Ala Arg Phe Thr Ser Tyr Ile Lys Ser Ile
 65                  70                  75                  80

Arg Gln Ser His Asn Leu Glu Asp Lys Ile Asp Thr Leu Glu Pro Asp
                 85                  90                  95

Thr Asn Leu Lys Leu Thr Ala Gln Glu Val Gln Gln Phe Glu Ala Lys
```

```
            100                 105                 110
Ile Ala Gln Asn Ile Pro Asp Leu Asp Asn Thr Leu Leu Val Leu Val
        115                 120                 125

Asp Gly Phe Met Leu Phe His Asp Arg Glu Ile Ile Gln Leu Phe Asp
    130                 135                 140

Val Lys Leu Phe Phe His Ala Ser Phe Glu Thr Leu Lys Asn Arg Arg
145                 150                 155                 160

Glu Ser Arg Lys Gly Tyr Asn Thr Val Glu Gly Phe Trp Val Asp Pro
                165                 170                 175

Pro Asn Tyr Phe Arg Asp Met Val Trp Pro Ala Tyr Glu Ser Ser His
            180                 185                 190

Lys Tyr Leu Phe Glu Asn Lys Asp Val Asp Gly Val Leu Lys Ser Glu
        195                 200                 205

Tyr Lys Thr Gln Tyr Gln Ile His Asp Ile Arg Asn Glu Thr Gly Val
    210                 215                 220

Lys Leu Tyr Glu Val Val Asp Trp Ser Leu Gln His Ile Phe Ala Met
225                 230                 235                 240

Val Lys Arg Leu

<210> SEQ ID NO 18
<211> LENGTH: 340
<212> TYPE: PRT
<213> ORGANISM: Saccharomyces cerevisiae

<400> SEQUENCE: 18

Met Thr Val Ser Lys Ile Pro Ile Trp Leu Asp Cys Asp Pro Gly His
1               5                   10                  15

Asp Asp Ala Ile Ala Ile Leu Leu Gly Cys Phe His Pro Ala Phe Asn
            20                  25                  30

Leu Leu Gly Ile Ser Thr Cys Phe Gly Asn Ala Pro Pro Glu Asn Thr
        35                  40                  45

Asp Tyr Asn Ala Arg Ser Leu Leu Thr Ala Met Gly Lys Ala Gln Ala
    50                  55                  60

Ile Pro Val Tyr Lys Gly Ala Gln Arg Pro Trp Lys Arg Glu Pro His
65                  70                  75                  80

Tyr Ala Pro Asp Ile His Gly Ile Ser Gly Leu Asp Gly Thr Ser Leu
                85                  90                  95

Leu Pro Lys Pro Thr Phe Glu Ala Arg Thr Asp Lys Thr Tyr Ile Glu
            100                 105                 110

Ala Ile Glu Glu Ala Ile Leu Ala Asn Asn Gly Glu Ile Ser Phe Val
        115                 120                 125

Ser Thr Gly Ala Leu Thr Thr Leu Ala Thr Val Phe Arg Cys Lys Pro
    130                 135                 140

Tyr Leu Lys Lys Ser Val Lys Tyr Ile Ser Ile Met Gly Gly Gly Leu
145                 150                 155                 160

His Gly Leu Gly Asn Cys Asn Pro Asn Leu Ser Ala Glu Phe Asn Val
                165                 170                 175

Trp Ile Asp Pro Asp Ala Ala Asn Tyr Ile Phe Arg Asp Pro Asp Val
            180                 185                 190

Lys Asp Lys Cys Ile Val Val Pro Leu Asn Leu Thr His Lys Ala Ile
        195                 200                 205

Ala Thr Tyr Lys Val Asn Glu Met Ile Tyr Asn Glu Lys Asn Asn Ser
    210                 215                 220

Lys Leu Arg Glu Leu Phe Leu Glu Leu Phe Gln Phe Phe Ala His Thr
225                 230                 235                 240
```

```
Tyr Lys Asp Met Gln Gly Phe Glu Ser Gly Pro Pro Ile His Asp Pro
                245                 250                 255

Val Ala Leu Met Pro Leu Leu Glu Phe Tyr Gly Trp Asp Pro Ser Ser
            260                 265                 270

Ala Val Gly Phe Arg Tyr Lys Arg Met Asp Ile Ser Cys Ile Asp Asp
        275                 280                 285

Val Phe Asn Glu Asn Ser Gly Lys Ile Ile Glu Lys Glu Tyr Pro
    290                 295                 300

Asn Asp Ser Asp Val Gly Thr Ile Ile Gly Leu Asp Leu Asn Ile Gln
305                 310                 315                 320

Tyr Phe Trp Asp Gln Ile Phe Glu Ala Leu Asn Arg Ala Asp Lys Met
                325                 330                 335

Ser Thr Ile Gly
            340

<210> SEQ ID NO 19
<211> LENGTH: 330
<212> TYPE: PRT
<213> ORGANISM: Schizosaccharomyces pombe

<400> SEQUENCE: 19

Met Thr Asn Thr Ile Asp Ser Phe Gln Lys Gly Ser Ala Leu Glu Asn
1               5                   10                  15

Tyr Asn Ile Trp Ile Asp Cys Asp Pro Gly His Asp Asp Val Val Ala
            20                  25                  30

Leu Thr Leu Ala Ala Cys Ala Gly His Cys Lys Ile Leu Gly Val Ser
        35                  40                  45

Thr Val His Gly Asn Thr Thr Leu Glu Phe Thr Thr Lys Asn Ala Leu
    50                  55                  60

Ala Val Met Glu Leu Leu Asn Gln Asp Val Asp Val His Ala Gly Ala
65                  70                  75                  80

Ala Lys Pro Leu Met Arg Glu Ser Ala Phe Ala Thr His Ile His Gly
                85                  90                  95

Thr Asn Gly Leu Ala Gly Ile Ser Leu Leu Pro Asp Tyr Pro Lys Lys
            100                 105                 110

Lys Ala Thr Pro Asp Ala Val Phe Ala Met Tyr Thr Thr Ile Ser Asn
        115                 120                 125

Tyr Pro Glu Pro Val Thr Leu Val Ala Thr Gly Pro Leu Thr Asn Ile
    130                 135                 140

Ala Leu Leu Leu Ala Thr Tyr Pro Ser Val Thr Asp Asn Ile Glu Arg
145                 150                 155                 160

Phe Ile Phe Met Gly Gly Ser Thr Gly Ile Gly Asn Ile Thr Ser Gln
                165                 170                 175

Ala Glu Phe Asn Val Tyr Ala Asp Pro Glu Ala Ala Arg Leu Val Leu
            180                 185                 190

Glu Thr Lys Ser Leu Ile Gly Lys Leu Phe Met Val Pro Leu Asp Val
        195                 200                 205

Thr His Lys Val Leu Leu Asp Ala Asn Ile Ile Gln Leu Leu Arg Gln
    210                 215                 220

His Ser Asn Pro Phe Ser Ser Thr Leu Val Glu Leu Met Thr Val Phe
225                 230                 235                 240

Gln Gln Thr Tyr Glu Asn Val Tyr Gly Ile Arg Asn Gly Val Pro Val
                245                 250                 255

His Asp Val Cys Ala Val Ala Leu Ala Leu Trp Pro Ser Leu Trp Thr
            260                 265                 270
```

```
Ser Arg Ser Met Tyr Val Thr Val Ser Leu Asp Ser Leu Thr Leu Gly
            275                 280                 285

Arg Thr Val Cys Asp Val Trp Ser Gln Gln Asn Gln Tyr Pro Ala Asn
290                 295                 300

Val His Val Val Leu Glu Ala Asp Val Ser Leu Phe Trp Glu Thr Phe
305                 310                 315                 320

Ile Gly Val Ile Asp Arg Leu Asn Tyr Leu
            325                 330

<210> SEQ ID NO 20
<211> LENGTH: 338
<212> TYPE: PRT
<213> ORGANISM: Kluyveromyces lactis

<400> SEQUENCE: 20

Met Thr Gly Asn Ser Val Ile Pro Ile Trp Val Asp Cys Asp Pro Gly
1               5                   10                  15

His Asp Asp Ala Val Ala Ile Leu Leu Ser Cys Phe His Pro Ser Ile
                20                  25                  30

Arg Leu Leu Gly Ile Ser Ala Ser Tyr Gly Asn Ala Ser Pro Glu Asn
            35                  40                  45

Thr Leu Tyr Asn Thr Leu Ser Leu Leu Thr Ala Phe Gly Lys Gln Asp
        50                  55                  60

Glu Val Pro Val Tyr Lys Gly Ala Gln Arg Pro Trp Val Arg Asp Val
65                  70                  75                  80

Ala Tyr Ala Pro Asp Ile His Gly Glu Thr Gly Leu Asp Gly Thr Thr
                85                  90                  95

Leu Leu Pro Lys Pro Lys Arg Ser Phe Val Asp Ala Asp Tyr Ile Lys
            100                 105                 110

Ala Met Glu Asn Ala Ile Leu Ala Asn Gly Gly Asn Ile Ala Leu Val
        115                 120                 125

Ser Thr Gly Thr Leu Thr Ser Ile Ala Thr Leu Phe Lys Glu Lys Pro
130                 135                 140

Tyr Leu Lys Glu Gln Val Arg Tyr Ile Ser Ile Met Gly Gly Gly Leu
145                 150                 155                 160

His Ala Gly Asn Arg Asn Asp Asn Asp Ser Ala Glu Phe Asn Ile Trp
                165                 170                 175

Ala Asp Pro Asp Ala Ala Asp Phe Ile Leu Asn Asp Glu Asp Ile Lys
            180                 185                 190

His Lys Cys Ile Leu Ser Pro Leu Asp Leu Thr His Thr Cys Ile Ala
        195                 200                 205

Thr Glu Tyr Ile Asp Lys Thr Ile Leu Gly Asp Gly Ser Cys Lys Leu
210                 215                 220

Arg Lys Leu Phe Tyr Glu Leu Phe Leu Phe Ala Lys Thr Tyr Lys
225                 230                 235                 240

Asn Lys Gln Gly Phe Glu Ala Gly Pro Pro Val His Asp Pro Val Thr
                245                 250                 255

Leu Met Pro Leu Leu Tyr Leu Tyr Gly His Ile Ser Asn Asp Ile Leu
            260                 265                 270

Arg Phe Lys Tyr Gly Arg Phe Asp Leu Ser Ile Asp Lys Asn Gln Asp
        275                 280                 285

Ser Ile Asn Tyr Gly Arg Thr Ile Val Thr Gln Glu Tyr Pro Ser Asp
290                 295                 300

Ser Asn Phe Gly Leu Met Val Gly Leu Gln Ile Asn Val Asp Phe Phe
305                 310                 315                 320
```

Trp Asn Gln Val Leu Asn Ala Ile Asp Val Ala Glu Asn Tyr Pro Gly
                325                 330                 335

Ser Leu

<210> SEQ ID NO 21
<211> LENGTH: 375
<212> TYPE: PRT
<213> ORGANISM: Aspergillus oryzae

<400> SEQUENCE: 21

Met His Ser Ser Asp Ile Pro Ile Pro Leu Trp Leu Asp Cys Asp
1               5                   10                  15

Pro Gly His Asp Asp Ala Phe Ala Ile Leu Leu Ala Ala His His Pro
                20                  25                  30

Ser Leu Asn Leu Leu Gly Ile Thr Thr Val His Gly Asn Ala Ser Leu
            35                  40                  45

Glu Asn Thr Thr Asn Asn Ala Thr Arg Ile Leu Glu Ala Ile Gly Arg
        50                  55                  60

Pro Glu Ile Pro Val Tyr Pro Gly His Lys Lys Pro Phe Cys Arg Pro
65                  70                  75                  80

Ala Ile His Ala Pro Asn Ile His Gly Asp Ser Gly Ile Asp Gly Thr
                85                  90                  95

Glu Leu Leu Pro Lys Ala Thr Lys Ser Pro Ile Thr Asp Lys Asn Pro
            100                 105                 110

Ile Leu Ala Met Arg Asp Ala Leu Leu Ala Gln Pro Lys Gly Thr Pro
        115                 120                 125

Trp Val Ile Ala Thr Gly Thr Leu Thr Asn Val Ala Leu Leu Phe Ala
130                 135                 140

Thr Phe Pro Glu Val Ala Glu His Ile Gln Gly Leu Ser Ile Met Gly
145                 150                 155                 160

Gly Gly Val Gly Gly Phe Thr Asp Ala Pro Met Ser Arg Leu Val
                165                 170                 175

Gly Glu Glu Ser Arg Ile Gly Asn Ile Thr Pro Leu Ala Glu Phe Asn
            180                 185                 190

Ile Tyr Cys Asp Pro Glu Ala Ser Gln Ser Ile Phe Ser Asn Pro Val
        195                 200                 205

Leu Ala Ser Lys Thr Thr Leu Ile Thr Leu Asp Leu Thr His Gln Val
210                 215                 220

Leu Ala Ser His Ser Val Gln Ser Arg Val Leu His Gly Gly Asp Asp
225                 230                 235                 240

Leu Ser Val Pro Pro Thr Val Leu Arg Gln Met Leu Phe Asp Leu Leu
                245                 250                 255

Val Phe Phe Ala Ser Thr Tyr Glu Asn Val Phe Gly Leu Thr Ser Gly
            260                 265                 270

Pro Pro Leu His Asp Pro Leu Ala Val Ala Val Ile Leu Ser Thr Leu
        275                 280                 285

Asn Pro Glu Tyr Ala Lys Arg His Pro Asp Gln Val Leu Lys Phe Asp
    290                 295                 300

Asp Arg Asn Gly Glu Arg Phe Asp Val Asp Val Thr Asp Gly Leu
305                 310                 315                 320

His Gly Thr Asp Val Glu Leu Val Gly Glu Leu Gly Arg Ser Lys Val
                325                 330                 335

Ile Ser Gly Thr Thr Gly Val Ala Ile Pro Arg Gly Val Asp Leu Asp
            340                 345                 350

```
Ala Phe Trp Asn Met Ile Leu Asp Cys Leu Arg Arg Ala Asp Glu Cys
        355                 360                 365

Asn Ala Ala Arg Lys Leu Ala
    370                 375

<210> SEQ ID NO 22
<211> LENGTH: 348
<212> TYPE: PRT
<213> ORGANISM: Pichia stipitis

<400> SEQUENCE: 22

Met Thr Val Gly Glu Lys Ile Pro Ile Trp Leu Asp Cys Asp Pro Gly
1               5                   10                  15

Asn Asp Asp Ala Phe Ala Ile Leu Leu Ala Leu Phe Asp Pro Arg Phe
            20                  25                  30

Glu Leu Leu Gly Ile Ser Thr Val His Gly Asn Ala Pro Leu Ser Tyr
        35                  40                  45

Thr Thr His Asn Ala Leu Ser Leu Leu Asp Ser Leu Gly Val Glu Pro
    50                  55                  60

Gly Thr Val Lys Val Tyr Ala Gly Ser Glu Thr Pro Leu Val Asn Ala
65                  70                  75                  80

Pro Gln Ser Ala Pro Glu Ile His Gly Thr Thr Gly Ile Gly Gly Val
                85                  90                  95

Glu Phe Pro Glu Val Thr Lys Asn Lys Val Ala Thr Val Gly Tyr
            100                 105                 110

Leu Glu Ala Met Lys Gln Ala Ile Leu Ser His Glu Asn Glu Leu Cys
        115                 120                 125

Leu Val Cys Thr Gly Thr Leu Thr Asn Val Ser Lys Leu Ile Thr Glu
    130                 135                 140

Cys Pro Ala Ile Ile Pro Lys Ile Arg Tyr Val Ser Ile Met Gly Gly
145                 150                 155                 160

Ala Phe Asn Leu Gly Asn Val Thr Pro Tyr Ala Glu Phe Asn Phe Tyr
                165                 170                 175

Ala Asp Pro His Ala Ala Lys His Val Leu Ala Glu Leu Gly Pro Lys
            180                 185                 190

Ile Ile Leu Ser Pro Leu Asn Ile Thr His Lys Ala Thr Ala Thr Glu
        195                 200                 205

Ser Ile Arg Asn Gln Met Tyr Asp Ser Glu Asp Pro His Arg Asn Ser
    210                 215                 220

Asp Ile Arg Asn Met Phe Tyr Ser Ile Leu Met Phe Phe Ser His Ser
225                 230                 235                 240

Tyr Ile Lys Lys Tyr Gly Ile Thr Glu Gly Pro Pro Val His Asp Pro
                245                 250                 255

Leu Ala Leu Tyr Cys Leu Leu Pro Phe Leu Gln Gln Asp Lys Asp Tyr
            260                 265                 270

Lys Tyr Lys Tyr Leu Arg Arg Lys Val Ser Val Ile Thr Glu Gly Glu
        275                 280                 285

His Ser Gly Glu Ser Ile Leu Leu Asn Gly Asn Ser Asp Ser Ser Val
    290                 295                 300

Glu Glu Glu Asp Gly Val Tyr Ile Gly Gln Ile Asp Val Asp Gln
305                 310                 315                 320

Phe Trp Arg Thr Val Leu Arg Ala Val Asn Val Ala Asp Val Thr Ile
                325                 330                 335

Lys Gln Glu Ile Asn Gly Ala Gln Lys Val Met Val
            340                 345
```

-continued

<210> SEQ ID NO 23
<211> LENGTH: 311
<212> TYPE: PRT
<213> ORGANISM: Saccharomyces cerevisiae

<400> SEQUENCE: 23

Met Ser Asp Ile Leu Asn Val Ser Gln Gln Arg Glu Ala Ile Thr Lys
1               5                   10                  15

Ala Ala Ala Tyr Ile Ser Ala Ile Leu Glu Pro His Phe Lys Asn Thr
            20                  25                  30

Thr Asn Phe Glu Pro Pro Arg Thr Leu Ile Ile Cys Gly Ser Gly Leu
        35                  40                  45

Gly Gly Ile Ser Thr Lys Leu Ser Arg Asp Asn Pro Pro Val Thr
    50                  55                  60

Val Pro Tyr Gln Asp Ile Pro Gly Phe Lys Lys Ser Thr Val Pro Gly
65                  70                  75                  80

His Ser Gly Thr Leu Met Phe Gly Ser Met Asn Gly Ser Pro Val Val
                85                  90                  95

Leu Met Asn Gly Arg Leu His Gly Tyr Glu Gly Asn Thr Leu Phe Glu
            100                 105                 110

Thr Thr Phe Pro Ile Arg Val Leu Asn His Met Gly His Val Arg Asn
        115                 120                 125

Leu Ile Val Thr Asn Ala Ala Gly Gly Ile Asn Ala Lys Tyr Gln Ala
130                 135                 140

Cys Asp Leu Met Cys Ile Tyr Asp His Leu Asn Ile Pro Gly Leu Ala
145                 150                 155                 160

Gly Gln His Pro Leu Arg Gly Pro Asn Leu Asp Glu Asp Gly Pro Arg
                165                 170                 175

Phe Leu Ala Leu Ser Asp Ala Tyr Asp Leu Glu Leu Arg Lys Leu Leu
            180                 185                 190

Phe Lys Lys Trp Lys Glu Leu Lys Ile Gln Arg Pro Leu His Glu Gly
        195                 200                 205

Thr Tyr Thr Phe Val Ser Gly Pro Thr Phe Glu Thr Arg Ala Glu Ser
    210                 215                 220

Lys Met Ile Arg Met Leu Gly Gly Asp Ala Val Gly Met Ser Thr Val
225                 230                 235                 240

Pro Glu Val Ile Val Ala Arg His Cys Gly Trp Arg Val Leu Ala Leu
                245                 250                 255

Ser Leu Ile Thr Asn Thr Cys Val Val Asp Ser Pro Ala Ser Ala Leu
            260                 265                 270

Asp Glu Ser Pro Val Pro Leu Glu Lys Gly Lys Ala Thr His Ala Glu
        275                 280                 285

Val Leu Glu Asn Gly Lys Ile Ala Ser Asn Asp Val Gln Asn Leu Ile
    290                 295                 300

Ala Ala Val Met Gly Glu Leu
305                 310

<210> SEQ ID NO 24
<211> LENGTH: 315
<212> TYPE: PRT
<213> ORGANISM: Schizosaccharomyces pombe

<400> SEQUENCE: 24

Met Thr Ala Thr Ser Phe Leu His Gln Ala Lys Gln Gln Pro His His
1               5                   10                  15

Thr Glu Pro Tyr Ile Lys Ala Leu Glu Ala Arg Glu Tyr Ile Ile Glu

```
                20                  25                  30
Gln Val Pro Glu Glu Leu Ser Lys Pro Lys Val Ala Ile Ile Cys Gly
                35                  40                  45

Ser Gly Leu Gly Thr Leu Ala Ser Gly Leu Ser Ala Pro Val Tyr Glu
        50                  55                  60

Val Pro Tyr Glu Asp Ile Pro His Phe His Val Ser His Val Pro Gly
65                  70                  75                  80

His Ala Ser Lys Leu Tyr Phe Ala Phe Leu Gly Glu Lys Arg Val Pro
                85                  90                  95

Thr Met Ile Leu Ala Gly Arg Tyr His Ser Tyr Glu Gly Tyr Pro Ile
            100                 105                 110

Glu Ala Thr Thr Phe Pro Val Arg Leu Met Lys Val Met Gly Val Glu
            115                 120                 125

Val Met Val Val Thr Asn Ala Ala Gly Gly Leu Asn Gln Gly Phe Lys
130                 135                 140

Val Gly Asp Leu Met Ile Leu Lys Asp His Ile Asn Phe Pro Gly Leu
145                 150                 155                 160

Ala Gly Met Asn Pro Leu Arg Gly Pro Asn Ala His Glu Phe Gly Val
                165                 170                 175

Arg Phe Pro Pro Leu Ser Asp Ala Tyr Asp Leu Glu Leu Arg Lys Leu
            180                 185                 190

Val Tyr Asp Ala Ala Lys Ala His Lys Val Ser Arg Thr Ile His Glu
            195                 200                 205

Gly Cys Tyr Ala Phe Val Ser Gly Pro Cys Phe Glu Thr Arg Ala Glu
        210                 215                 220

Ser Arg Met Leu Ala Leu Met Gly Ala Asp Cys Val Gly Met Ser Thr
225                 230                 235                 240

Val Pro Glu Val Val Val Ala Arg His Cys Gly Ile Arg Val Leu Ala
                245                 250                 255

Ile Ser Leu Val Thr Asn Asn Val Val Glu Glu Ser Pro Ser Ala
            260                 265                 270

Lys Asp Leu Val Glu Val Asp Ser Asn Val Met Ser Lys Gly Ala Ala
            275                 280                 285

Asn His Leu Glu Val Leu Glu Val Gly Ile Ala Ala Ala Asp Val
290                 295                 300

Arg Thr Met Val Glu Thr Ile Val Asn Phe Ile
305                 310                 315

<210> SEQ ID NO 25
<211> LENGTH: 306
<212> TYPE: PRT
<213> ORGANISM: Kluyveromyces lactis

<400> SEQUENCE: 25

Met Ser Ser Leu Asp Ile Asn Glu Gln Arg Ala Leu Ile Lys Ser Ala
1               5                   10                  15

His Arg Tyr Ile Ser Glu Lys Leu Glu Asp His Phe Ser Ser Glu Phe
                20                  25                  30

Leu Pro Lys Ala Leu Val Ile Cys Gly Ser Gly Leu Ser Gly Ile Ser
            35                  40                  45

Thr Lys Ile Ala Asp Glu Pro Lys Pro Leu Ile Leu Ser Tyr Ser Thr
        50                  55                  60

Ile Pro Gly Phe Lys Val Ser Thr Val Pro Gly His Ser Gly Glu Leu
65                  70                  75                  80

Ile Phe Gly Tyr Met Asn Gly Ala Pro Val Val Leu Met Asn Gly Arg
```

```
                        85                  90                  95
Leu His Ser Tyr Glu Gly His Ser Leu Ala Glu Thr Val His Pro Ile
                    100                 105                 110

Arg Ala Leu His Leu Leu Gly Ser Ile Asn Val Leu Ile Val Thr Asn
                115                 120                 125

Ala Ala Gly Gly Ile Asn Ala Ser Phe Lys Ala Gly Asp Leu Met Cys
            130                 135                 140

Val Tyr Asp His Ile Asn Phe Pro Gly Leu Cys Gly Phe His Pro Leu
145                 150                 155                 160

Arg Gly Ala Asn Phe Asp Glu Phe Gly Pro Arg Phe Leu Ala Thr Ser
                165                 170                 175

Asp Ala Tyr Asp Leu Glu Leu Arg Lys Leu Leu Phe Ser Lys Lys Lys
                180                 185                 190

Glu Leu Asn Ile Glu Arg Lys Ile His Glu Gly Thr Tyr Ser Tyr Val
                195                 200                 205

His Gly Pro Thr Phe Glu Ser Arg Ala Glu Ser Arg Phe Leu Arg Leu
            210                 215                 220

Ala Gly Thr Asp Ala Val Gly Met Ser Thr Val Pro Glu Val Val Thr
225                 230                 235                 240

Ala Arg His Cys Gly Trp Arg Val Leu Ala Leu Ser Leu Ile Thr Asn
                245                 250                 255

Glu Cys Val Val Asp Pro Pro Ala Ser Ala His Asp Glu Asn Pro Val
                260                 265                 270

Pro Ile Gln Glu Gly Lys Ala Thr His Glu Glu Val Leu Glu Asn Ser
                275                 280                 285

Ala Lys Ala Ser Lys Asp Val Gln Glu Leu Ile Phe Ser Val Val Ala
            290                 295                 300

Glu Ile
305

<210> SEQ ID NO 26
<211> LENGTH: 598
<212> TYPE: PRT
<213> ORGANISM: Saccharomyces cerevisiae

<400> SEQUENCE: 26

Met Ser Phe Ser Ser Ile Val Ser Lys Phe Leu Arg Tyr Leu Glu Ile
1               5                   10                  15

Pro Ala Lys Asn Arg Thr Ala Val Asn Phe Leu Arg Asn Pro Asp Leu
                20                  25                  30

Gln Pro Ile Lys Ser Ala Asn Gln Thr Trp Gly Phe Trp Ser Asn Leu
            35                  40                  45

Ala Tyr Trp Gly Ala Val Ser Phe Thr Ala Gly Thr Trp Met Ser Gly
        50                  55                  60

Ser Ala Ala Leu Ser Val Gly Leu Ser Tyr Pro Glu Thr Ile Val Ser
65                  70                  75                  80

Phe Leu Leu Gly Asn Val Leu Thr Ile Ile Phe Thr Met Ala Asn Ser
                85                  90                  95

Tyr Pro Gly Tyr Asp Trp Lys Ile Gly Phe Thr Leu Ala Gln Arg Phe
                100                 105                 110

Val Phe Gly Ile Tyr Gly Ser Ala Phe Gly Ile Ile Arg Ile Leu
            115                 120                 125

Met Ser Ile Val Asn Tyr Gly Ser Asn Ala Trp Leu Gly Gly Leu Ser
        130                 135                 140

Ile Asn Met Ile Leu Asp Ser Trp Ser His His Tyr Leu His Leu Pro
```

-continued

```
            145                 150                 155                 160
Asn Thr Leu Ser Pro Ser Val Ala Met Thr Thr Lys Gln Leu Val Gly
                165                 170                 175
Phe Ile Ile Phe His Val Leu Thr Ala Leu Cys Tyr Phe Met Lys Pro
            180                 185                 190
Tyr His Met Asn Tyr Leu Leu Ile Trp Ser Cys Val Ala Thr Cys Phe
        195                 200                 205
Ala Met Leu Gly Ile Val Ile Tyr Leu Thr Lys Asn Ala His Gly Val
    210                 215                 220
Gly Glu Leu Phe Thr Ser Thr Lys Ser Thr Val Thr Gly Ser Lys Arg
225                 230                 235                 240
Ala Trp Ala Trp Val Tyr Met Ile Ser Tyr Trp Phe Gly Ser Ile Ser
                245                 250                 255
Pro Gly Ser Thr Asn Gln Ser Asp Tyr Ser Arg Phe Gly Ser Ser Asn
                260                 265                 270
Leu Ala Ile Trp Thr Gly Ser Val Cys Ala Leu Leu Ile Pro Ala Thr
            275                 280                 285
Leu Val Pro Ile Phe Gly Val Ile Ser Ala Ser Thr Cys Asp Lys Leu
        290                 295                 300
Tyr Gly Lys Gln Phe Trp Met Pro Met Asp Ile Phe Asp Tyr Trp Leu
305                 310                 315                 320
Thr Asn Asn Tyr Ser Ala Gly Ala Arg Ala Gly Ala Phe Phe Cys Gly
                325                 330                 335
Leu Cys Phe Thr Met Ser Gln Met Ser Ser Thr Ile Ser Asn Cys Gly
            340                 345                 350
Phe Ala Thr Gly Met Asp Met Ala Gly Leu Leu Pro Lys Tyr Val Asp
        355                 360                 365
Ile Lys Arg Gly Ala Leu Phe Cys Ala Cys Ile Ser Trp Ala Cys Leu
    370                 375                 380
Pro Trp Asn Phe Tyr Asn Ser Ser Ser Thr Phe Leu Thr Val Met Ser
385                 390                 395                 400
Ser Phe Gly Val Val Met Thr Pro Ile Ile Ala Val Met Ile Cys Asp
                405                 410                 415
Asn Phe Leu Ile Arg Lys Arg Gln Tyr Ser Ile Thr Asn Ala Phe Ile
            420                 425                 430
Leu Lys Gly Glu Tyr Tyr Phe Thr Lys Gly Val Asn Trp Arg Ala Ile
        435                 440                 445
Val Ala Trp Val Cys Gly Met Ala Pro Gly Leu Pro Gly Ile Ala Trp
    450                 455                 460
Glu Val Asn Asn Asn Tyr Phe His Asp Ser Gly Ile Val Lys Phe Phe
465                 470                 475                 480
Tyr Gly Asp Ser Phe Phe Ser Phe Leu Ile Ser Phe Val Tyr Trp
                485                 490                 495
Gly Leu Cys Val Phe Phe Pro Phe Lys Ile Thr Val Arg His Asp Asp
            500                 505                 510
Lys Asp Tyr Tyr Gly Ala Phe Thr Asp Glu Glu Ala Arg Lys Lys Gly
        515                 520                 525
Met Ile Pro Tyr Ser Glu Ile Ser Glu Glu Ile Arg Ala Tyr Thr
    530                 535                 540
Leu Gly Glu Cys Tyr Thr Thr Gly His Glu Tyr Lys Pro Glu Ser Ser
545                 550                 555                 560
Asp Asn Glu Ser Pro Glu Leu Ile Lys Thr Ser Ser Glu Asn Thr Asn
                565                 570                 575
```

-continued

```
Val Phe Glu Ile Val His Gln Lys Asp Asp Glu Lys His Ser Phe Ser
            580                 585                 590

Thr Thr Gln Gln Val Val
        595
```

<210> SEQ ID NO 27
<211> LENGTH: 559
<212> TYPE: PRT
<213> ORGANISM: Schizosaccharomyces pombe

<400> SEQUENCE: 27

```
Met Glu Asp Pro Lys Ser Asp Glu Lys Phe Asp Ile Gly Ile Ser Glu
1               5                   10                  15

Lys Asn Leu Asp Val Gly Phe Gly Glu Ser Ser Val Asp Val Pro
            20                  25                  30

Val Lys Gly Arg Phe Ala Ser Phe Leu Lys Lys Leu Glu Leu Ser Ser
        35                  40                  45

Gly Pro Glu Lys Glu Asn Ile Asp Leu Arg Pro Thr Pro Pro Asp Arg
    50                  55                  60

Arg His Tyr Ser Ala Leu Asp Ile Ile Tyr Leu Trp Ser Cys Asn Gly
65                  70                  75                  80

Ile Ser Ala Ser Ala Phe Arg Thr Gly Thr Ser Tyr Met Glu Met Gly
                85                  90                  95

Leu Ser Pro Lys Gln Ala Leu Ala Ala Leu Ile Ala Gly Asn Val Phe
            100                 105                 110

Ile Ala Met Pro Met Thr Leu Asn Gly Leu Phe Gly Ser His Tyr His
        115                 120                 125

Ile Pro Phe Ala Val Gln Ser Arg Ala Ser Phe Gly Tyr Tyr Phe Asn
    130                 135                 140

Thr Leu Ile Ile Leu Leu Arg Phe Ile Ala Gly Leu Phe Tyr Tyr Gly
145                 150                 155                 160

Thr Asn Val Tyr Thr Gly Ala Glu Cys Val Gln Thr Ile Leu Tyr Ala
                165                 170                 175

Ile Phe Lys Ser Phe Arg Ser Tyr Lys Asn Arg Leu Pro Ala Asp Ala
            180                 185                 190

Gly Ile Thr Ser Asp Phe Leu Ile Ser Tyr Phe Val Tyr Trp Val Ile
        195                 200                 205

Ser Phe Pro Phe His Leu Ile Arg Pro Glu Tyr Leu Gln Arg Phe Phe
    210                 215                 220

Leu Ile Lys Ser Ile Ser Thr Tyr Ile Ala Cys Phe Ala Met Leu Ile
225                 230                 235                 240

Phe Leu Leu Cys Asn Val Gly Ser His Val Val Trp Asp Gln Pro Ala
                245                 250                 255

Thr Val Ser Gly Arg Ser Trp Ser Trp Val Phe Met Cys Ala Leu Asn
            260                 265                 270

Ser Ser Val Ala Gly Phe Ser Thr Leu Ala Val Asn Val Asn Asp Phe
        275                 280                 285

Thr Arg Tyr Val Lys His Pro Lys Thr Pro Tyr Val Gln Met Leu Ile
    290                 295                 300

Leu Pro Leu Val Ala Ala Val Ser Ala Pro Ile Gly Ile Val Ser Gly
305                 310                 315                 320

Val Ala Ser Lys Ile Met Tyr Gly Thr Ala Met Trp Asp Pro Leu Gln
                325                 330                 335

Ile Ala Asn Asn Trp Thr Ser Arg Gly Gly Arg Ala Ala Phe Phe
            340                 345                 350
```

```
Met Gly Leu Thr Tyr Leu Val Ser Met Ile Ala Gln Asn Ile Ser Asp
            355                 360                 365

Asn Thr Val Ala Ala Ala Asn Asp Leu Leu Tyr Phe Phe Pro Arg Tyr
    370                 375                 380

Leu Asp Ile Arg Arg Ala Gln Val Ile Val Ile Ile Gly Ala Trp
385                 390                 395                 400

Ala Ile Val Pro Trp Lys Ile Leu Gln Asn Gly Thr Ala Phe Leu Ala
                405                 410                 415

Phe Leu Gly Ser Leu Ser Ile Phe Leu Gly Pro Ala Ala Gly Ile Phe
            420                 425                 430

Val Ala Asp Lys Phe Lys Asn His His Lys Tyr Asp Ile Asp Glu Phe
            435                 440                 445

Tyr Asn Pro Ser Gly Ile Tyr Arg Tyr Asn Lys Leu Gly Leu Asn Trp
    450                 455                 460

Arg Ala Leu Ile Ala Phe Leu Cys Ala Cys Val Pro Leu Ile Pro Gly
465                 470                 475                 480

Met Ala Met Ser Ile Asn Pro Ser Ile Thr Met Pro Asp Gly Val Ile
                485                 490                 495

His Leu Tyr Tyr Ile Gly Tyr Phe Tyr Ser Phe Met Thr Ala Phe Leu
            500                 505                 510

Ile Tyr Trp Gly Leu Asn Leu Val Phe Pro Ala Lys Glu Thr Leu Leu
            515                 520                 525

Glu Glu Ala Val Tyr Pro Pro Lys Ser Asn Ala Glu Leu Val Asp Pro
            530                 535                 540

Ser Thr Leu Ser Gly Lys Asp Lys Phe Trp Tyr Tyr Ile Asp Tyr
545                 550                 555

<210> SEQ ID NO 28
<211> LENGTH: 579
<212> TYPE: PRT
<213> ORGANISM: Kluyveromyces lactis

<400> SEQUENCE: 28

Met Ala Gly Val Leu Gly Lys Leu His Asn Leu Leu Val Leu Asp Glu
1               5                   10                  15

Ser Asp Arg Thr Ser Asn Lys Asp Leu Val Pro Met Pro Val Ser Arg
                20                  25                  30

Arg Lys Trp Gly Ile Tyr Gly Phe Thr Ser Tyr Trp Thr Leu Leu Cys
            35                  40                  45

Leu Cys Ile Ser Thr Trp Ser Gly Gly Ser Ala Leu Leu Leu Tyr Asp
        50                  55                  60

Val Gly Thr Asp Gly Glu Leu Thr Leu Ser Gly Met Asn Gly Arg Gln
65                  70                  75                  80

Thr Ile Gly Cys Ile Val Leu Ala Asn Phe Phe Ile Ser Ile Ala Ala
                85                  90                  95

Ile Ile Asn Ser Val Tyr Gly Ser Glu Tyr His Ile Gly Tyr Ser Val
                100                 105                 110

Phe Gln Arg Ile Ile Phe Gly Met Arg Gly Ser Ser Phe Gly Val Leu
            115                 120                 125

Ile Arg Ala Ile Leu Ser Val Val Trp Phe Ala Ser Gln Ala Trp Leu
        130                 135                 140

Gly Gly Leu Cys Val Asn Val Ile Ser Ser Trp Ser Glu Thr Tyr
145                 150                 155                 160

Leu Asn Leu Pro Asn Thr Phe Pro Glu Ser Val Pro Met Thr Arg Gln
                165                 170                 175
```

```
Glu Leu Ile Gly Phe Val Ile Phe Leu Val Ile Asn Thr Pro Val Leu
                180                 185                 190
Met Ile Arg Pro Glu Tyr Phe Asp His Ile Leu Ala Leu Gly Ser Phe
            195                 200                 205
Cys Met Phe Phe Val Gly Leu Gly Ile Thr Ile Trp Ala Val Thr Ile
210                 215                 220
Asn Gly Gly Ser Asn Gly Pro Leu Leu Thr Ala Lys Val Thr Ala Ser
225                 230                 235                 240
Ser Ser Asp Leu Ala Trp Ser Trp Ile Thr Asn Leu Asn Ala Trp Tyr
                245                 250                 255
Ser Phe Ile Ile Ala Gly Ile Ser Asn Gln Ser Asp Phe Ser Arg Phe
                260                 265                 270
Asn Lys Arg Pro Arg Ser Ala Tyr Ile Gly Ile Leu Ile Gly Val Asn
            275                 280                 285
Val Met Gly Ile Val Leu Pro Leu Met Gly Ile Val Thr Ala Ser Ala
            290                 295                 300
Leu Leu Glu Lys Tyr Gly Glu Ser Phe Trp Met Pro Asn Asp Ile Cys
305                 310                 315                 320
Met Tyr Trp Met Gln Leu Asn Tyr Thr Pro Lys Ser Arg Ala Ala Ala
                325                 330                 335
Phe Phe Ala Gly Leu Gly Leu Leu Ile Ser Gln Leu Gly Val Asn Cys
                340                 345                 350
Ile Ser Asn Ala Ile Ser Gly Gly Met Asp Leu Ala Ser Ile Phe Pro
            355                 360                 365
Arg Tyr Ile Asn Ile Arg Arg Gly Ser Ile Leu Ile Met Leu Leu Ala
            370                 375                 380
Trp Pro Thr Gln Pro Trp Leu Phe Tyr Asn Ala Thr Ser Thr Phe Leu
385                 390                 395                 400
Thr Val Met Ser Ser Phe Thr Val Phe Ile Thr Pro Leu Thr Ala Met
                405                 410                 415
Phe Val Cys Asp Tyr Phe Val Ile Arg Lys Gly Val Ile Lys Leu Ser
                420                 425                 430
Asp Cys Tyr Asp Ser Pro Ser Ile Tyr Trp Phe Gln Tyr Gly
            435                 440                 445
Ile Asn Trp Lys Asn Ile Leu Cys Phe Leu Cys Gly Ala Ala Pro Gly
450                 455                 460
Leu Pro Gly Leu Ile Asn Ala Ala Asn Pro Asn Ile Pro Ile Asn Thr
465                 470                 475                 480
Gly Ile Glu His Phe Phe Gln Gly Ser Phe Ile Phe Gln Phe Ala Val
                485                 490                 495
Thr Phe Ala Leu Tyr Tyr Ile Leu Asn Thr Ile Phe Lys Pro Thr Val
                500                 505                 510
Gly Glu Thr Asp Gln Ile Asp Tyr Tyr His Thr Phe Thr Glu Arg Glu
                515                 520                 525
Leu Gln Glu Lys Asn Met Ile Ala Asp Gln Glu Asp Ile Gly Val
            530                 535                 540
His Ser Ile Asp Ser Ser Asn Tyr Leu Ala Asp Pro Thr Glu Val Ser
545                 550                 555                 560
Leu Arg Asn Leu Lys Ile Asn Ser Pro Glu Lys Ser Asp Ser Thr Asp
                565                 570                 575
Val Val Leu

<210> SEQ ID NO 29
<211> LENGTH: 543
```

```
<212> TYPE: PRT
<213> ORGANISM: Aspergillus oryzae

<400> SEQUENCE: 29

Met Gly Arg Phe Ser Gly Ala Ala Ser Arg Leu His Arg Thr Leu Gln
1               5                   10                  15

Leu Ser Gly Asp Thr Asp Gln Trp Arg Asn Arg Asp Leu Ile Pro Leu
            20                  25                  30

Pro Pro Asp Arg Thr Thr Trp Ser Trp Asp Phe Leu Tyr Leu Trp
        35                  40                  45

Ser Thr Val Phe Phe Thr Thr Phe Gly Trp Gln Ile Thr Ser Ser Leu
    50                  55                  60

Leu Gly Leu Gly Leu Asn Val Trp Gln Ser Ile Leu Cys Asn Ile Ile
65                  70                  75                  80

Thr Lys Phe Leu Gln Thr Ala Val Val Phe Cys Val Ala Trp Pro Gly
                85                  90                  95

Gly Val Trp His Ile Gly Phe Thr Val Asn Ser Arg Ser Val Phe Gly
            100                 105                 110

Met Trp Gly Ser Tyr Val Pro Val Ile Leu Arg Ile Phe Leu Cys Ile
        115                 120                 125

Ile Trp Tyr Gly Val Gln Ala Phe Thr Gly Gly Gln Leu Val Ala Ile
    130                 135                 140

Ile Leu Ser Thr Ile Phe Ser Gly Tyr His His Met Glu Asn Thr Leu
145                 150                 155                 160

Pro Glu Ser Ala His Met Thr Thr Lys Gln Phe Val Gly Tyr Val Ile
                165                 170                 175

Phe Asn Ile Ile Ser Leu Gly Leu Leu Trp Val Pro Pro Asp Lys Leu
            180                 185                 190

Lys Lys Pro Phe Lys Leu Ile Ala Ala Ile Asn Leu Leu Val Ile Leu
        195                 200                 205

Gly Leu Ala Ile Gly Leu Ile Ala Gly Ala Arg Gly Gly Ser Leu Gly
    210                 215                 220

Thr Leu Gln Thr Ser Gln Arg Thr Asp Asn Leu Gly Trp Thr Phe Ile
225                 230                 235                 240

His Gly Phe Ala Val Val Phe Ser Gly Asn Ala Val Gly Met Ala Ser
                245                 250                 255

His Ser Asp Phe Ser Arg Phe Ala Arg Arg Pro Gly Ala Gln Val Lys
            260                 265                 270

Gly Gln Leu Phe Ser Phe Leu Ile Ser Gly Asn Val Val Pro Ile Leu
        275                 280                 285

Gly Ile Phe Gly Thr Ala Ala Ala Lys Met Tyr Gly Asp Val Asn
    290                 295                 300

Glu Leu Gly Leu Trp Asn Pro Pro Asn Ile Leu Gln Met Trp Leu Asp
305                 310                 315                 320

Asn Gln Tyr His Asn Lys Ala Met Arg Ala Ala Phe Phe Val Ala
                325                 330                 335

Phe Gly Leu Thr Ser Ser Ile Met Ala Met Asn Ser Ile Glu Asn Gly
            340                 345                 350

Val Ser Gly Gly Met Asp Ile Ala Gly Leu Tyr Pro Arg Tyr Phe Asn
        355                 360                 365

Ile Arg Arg Gly Ser Tyr Leu Leu Ala Ala Ile Ser Val Val Ile Asn
    370                 375                 380

Pro Trp Gln Ile Ile Ala Asn Gly Ala Ile Phe Thr Asn Thr Leu Asn
385                 390                 395                 400
```

```
Ser Phe Gly Val Ile Leu Phe Pro Leu Met Gly Thr Met Val Ala Asp
                405                 410                 415

Tyr Tyr Val Val Arg Lys Gln Lys Leu Lys Leu Ser Asp Leu Tyr Arg
            420                 425                 430

Ala Asp Ala Ser Ser Ile Tyr Trp Phe Glu Gly Gly Phe Asn Trp Arg
            435                 440                 445

Ala Phe Thr Ala Trp Leu Val Gly Phe Ala Pro Ser Val Pro Gly Leu
            450                 455                 460

Ala Ala Leu Asn Pro His Asn Thr Gly Ile Pro Ile Gly Leu Thr Tyr
465                 470                 475                 480

Thr Phe Tyr Leu Trp Pro Ile Ala Gly Phe Ala Ser Phe Val Leu
                485                 490                 495

His Ala Gly Leu Cys Tyr Leu Ser Pro Pro Ala Gly Ile Gly Lys Val
                500                 505                 510

Asp Glu Gln Glu Phe His Asp Pro Met Tyr Ser Glu Arg Ser Asp Glu
                515                 520                 525

Met Gln Ser Gln Thr Ile Thr Ala Met Glu Lys Gly Gln His Arg
                530                 535                 540

<210> SEQ ID NO 30
<211> LENGTH: 575
<212> TYPE: PRT
<213> ORGANISM: Pichia stipitis

<400> SEQUENCE: 30

Met Asp Ala Leu Lys Lys Leu Asp Lys Trp Ile Ala Val Glu Asp Thr
1               5                   10                  15

Ser Thr Glu Arg Gly Glu Asp Gln Ile Arg Ser Asn Glu Asp Leu Asp
                20                  25                  30

Pro Thr Pro Ser Asp Arg Arg Thr Trp Lys Met Tyr Asn Tyr Ile Leu
            35                  40                  45

Ile Trp Ala Gln Ser Ala Phe Asn Val Asn Glu Trp Asn Thr Gly Ala
    50                  55                  60

Ser Leu Met Lys Ala Ser Gly Leu Pro Tyr Gly Gln Thr Ile Gly Ser
65                  70                  75                  80

Ala Ile Phe Ser Ile Phe Val Ala Val Ile Phe Thr Ile Ala Asn Ala
                85                  90                  95

Arg Ala Gly Ser Thr Tyr His Ile Gly Tyr Pro Thr Leu Ala Arg Ala
                100                 105                 110

Thr Phe Gly Val Tyr Gly Ala Tyr Phe Phe Val Ala Ala Arg Gly Phe
            115                 120                 125

Val Ala Ile Ile Trp Phe Ser Val Gln Ser Tyr Tyr Gly Ser Met Cys
130                 135                 140

Leu Asp Val Ala Leu Arg Cys Met Phe Gly His Lys Trp Leu Asp Leu
145                 150                 155                 160

Lys Asn His Leu Pro Ala Ser Ala Asp Val Gln Ser Arg Ile Leu Leu
                165                 170                 175

Ala Phe Phe Leu Phe Trp Leu Ile Gln Phe Pro Leu Met Phe Val His
            180                 185                 190

Pro Arg Gln Ile Arg His Phe Phe Thr Val Lys Ser Phe Val Leu Pro
        195                 200                 205

Cys Ala Thr Ile Gly Leu Leu Ile Phe Cys Val Lys Lys Gly His Gly
210                 215                 220

Pro Gly Asn Tyr Asp Leu Gly Leu Pro Ile Ser Thr Ser Ser Ser Ala
225                 230                 235                 240
```

-continued

```
Ile Gly Trp Gly Trp Met Ser Val Met Asn Ser Ile Phe Gly Thr Ile
                245                 250                 255

Ser Pro Met Ile Ile Asn Gln Pro Asp Ile Ala Arg Tyr Ala Lys Lys
            260                 265                 270

Pro Ser Asp Thr Ile Leu Pro Gln Ala Ile Gly Phe Val Leu Ala Lys
        275                 280                 285

Ile Met Ile Met Val Val Gly Met Val Ala Thr Ala Ser Ile Tyr Arg
    290                 295                 300

Ser Tyr Gly Glu Val Tyr Trp Asn Met Trp Asp Leu Met Asn Ala Ile
305                 310                 315                 320

Leu Asp His Ser Trp Asn Ala Gly Ala Arg Thr Gly Val Phe Phe Val
                325                 330                 335

Ala Val Ser Phe Gly Ile Gly Thr Ala Gly Thr Asn Ile Phe Gly Asn
            340                 345                 350

Ser Ile Pro Phe Ala Cys Asp Ile Thr Gly Leu Leu Pro Lys Tyr Phe
        355                 360                 365

Thr Ile Leu Arg Gly Gln Ile Val Val Ala Ile Leu Ala Trp Ala Ile
    370                 375                 380

Val Pro Trp Lys Phe Leu Thr Asp Ala Ala Lys Phe Leu Thr Phe Leu
385                 390                 395                 400

Gly Ser Tyr Ser Ile Phe Val Gly Pro Ile Leu Gly Cys Met Leu Ala
                405                 410                 415

Asp Tyr Tyr Phe Val Lys Arg Gly Asn Ile His Val Pro Ser Leu Phe
            420                 425                 430

Thr Lys Lys Ser Ser Gly Val Tyr His Tyr Val Tyr Gly Trp Asn Leu
        435                 440                 445

Trp Ala Cys Phe Ala Trp Ala Gly Ala Ala Ser Ile Cys Ile Pro Gly
    450                 455                 460

Leu Tyr Arg Ala Tyr Tyr Pro Glu Ser Leu Ser Ile Ser Ala Thr Arg
465                 470                 475                 480

Met Tyr Gln Met Gly Tyr Ile Leu Thr Thr Ile Ser Ser Met Val Phe
                485                 490                 495

Tyr Tyr Cys Leu Ser Leu Ile Phe Lys Pro Gln Ile Tyr Pro Glu Ala
            500                 505                 510

His Arg Asp Thr Pro Lys Thr Trp Glu Tyr Met Arg Thr Thr Asp Gly
        515                 520                 525

Phe Phe Glu Asp Asp Ser Pro Ile Gly Lys Val Gly Tyr Phe Gly Ser
    530                 535                 540

Val Asp Val Phe Thr Gly Glu Lys Val Asp Thr Ser Glu Gly Ser Ser
545                 550                 555                 560

Val Lys Thr Lys Ser Glu Lys Ile Leu Glu Thr Val Ser Ile Val
                565                 570                 575
```